(12) United States Patent
Raycheck et al.

(10) Patent No.: US 8,652,116 B2
(45) Date of Patent: Feb. 18, 2014

(54) PREFERENTIAL BEND STRUCTURE AND ARTICLES CONTAINING SAID STRUCTURE

(75) Inventors: Jeromy Thomas Raycheck, Lebanon, OH (US); Mark James Kline, Okeana, OH (US); Bruce William Lavash, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 1432 days.

(21) Appl. No.: 11/240,286

(22) Filed: Sep. 30, 2005

(65) Prior Publication Data

US 2007/0074381 A1    Apr. 5, 2007

(51) Int. Cl.
*A61F 13/475*    (2006.01)
*A61F 13/539*    (2006.01)
*A61F 13/62*     (2006.01)

(52) U.S. Cl.
USPC ............... 604/385.201; 604/385.01; 24/442

(58) Field of Classification Search
USPC ............ 604/385.01, 385.201, 385.19, 380, 604/385.24–385.3
See application file for complete search history.

(56) References Cited

U.S. PATENT DOCUMENTS

| | | | |
|---|---|---|---|
| 3,860,003 A | | 1/1975 | Buell |
| 4,326,528 A | * | 4/1982 | Ryan et al. ............. 604/385.26 |
| 4,515,595 A | | 5/1985 | Kievit et al. |
| 4,610,678 A | | 9/1986 | Weisman et al. |
| 4,673,402 A | | 6/1987 | Weisman et al. |
| 4,695,278 A | | 9/1987 | Lawson |
| 4,701,179 A | | 10/1987 | Kellenberger et al. |
| 4,738,675 A | * | 4/1988 | Buckley et al. ............. 604/380 |
| 4,834,735 A | | 5/1989 | Alemany et al. |
| 4,886,513 A | * | 12/1989 | Mason et al. ............ 604/385.31 |
| 4,888,231 A | | 12/1989 | Angstadt |
| 4,892,536 A | | 1/1990 | Desmarais et al. |
| 4,909,803 A | | 3/1990 | Aziz et al. |
| 4,990,147 A | | 2/1991 | Freeland |
| 5,037,416 A | | 8/1991 | Allen et al. |
| 5,137,537 A | | 8/1992 | Herron et al. |
| 5,147,345 A | | 9/1992 | Young et al. |
| 5,151,092 A | | 9/1992 | Buell et al. |
| 5,171,302 A | * | 12/1992 | Buell ........................ 604/385.23 |
| 5,197,959 A | * | 3/1993 | Buell ........................ 604/385.23 |
| 5,212,855 A | | 5/1993 | McGanty |

(Continued)

FOREIGN PATENT DOCUMENTS

| | | |
|---|---|---|
| EP | 1 078 617 A2 | 2/2001 |
| GB | 2296437 A * | 7/1996 |

(Continued)

OTHER PUBLICATIONS

PCT Search Report, mailed Feb. 14, 2007, 4 pages.

*Primary Examiner* — Melanie Hand
*Assistant Examiner* — Paula Craig
(74) *Attorney, Agent, or Firm* — Charles R. Matson; Laura L. Whitmer; Eric T. Addington

(57) ABSTRACT

A preferential bend structure may have a first face and an opposing second face. The preferential bend structure may include at least a base layer and an auxiliary layer, wherein a first deforming force applied to the first face results in a first deflection and a second deforming force applied to the second face results in a second deflection which is equal to the first deflection, and wherein the second deforming force is not equal to the first deforming force.

18 Claims, 32 Drawing Sheets

(56) References Cited

U.S. PATENT DOCUMENTS

| | | | |
|---|---|---|---|
| 5,221,274 A | 6/1993 | Buell et al. | |
| 5,260,345 A | 11/1993 | Desmarais et al. | |
| 5,269,775 A | 12/1993 | Freeland et al. | |
| 5,300,053 A * | 4/1994 | Genaro | 604/378 |
| 5,300,055 A * | 4/1994 | Buell | 604/385.23 |
| 5,342,338 A | 8/1994 | Roe | |
| 5,382,246 A * | 1/1995 | Kawano | 604/385.24 |
| 5,387,207 A | 2/1995 | Dyer et al. | |
| 5,397,316 A | 3/1995 | Lavon et al. | |
| 5,399,175 A * | 3/1995 | Glaug et al. | 604/385.101 |
| 5,505,719 A * | 4/1996 | Cohen et al. | 604/372 |
| 5,514,120 A * | 5/1996 | Johnston et al. | 604/378 |
| 5,540,976 A | 7/1996 | Shawver et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,150 A * | 1/1997 | Olsen et al. | 604/385.23 |
| 5,601,544 A * | 2/1997 | Glaug et al. | 604/385.28 |
| 5,625,222 A | 4/1997 | Yoneda et al. | |
| 5,662,634 A * | 9/1997 | Yamamoto et al. | 604/378 |
| 5,713,883 A * | 2/1998 | Hsieh | 604/385.01 |
| 5,810,796 A | 9/1998 | Kimura et al. | 604/365 |
| 5,858,011 A * | 1/1999 | Brown et al. | 604/385.23 |
| 5,865,823 A | 2/1999 | Curro | |
| 5,919,181 A * | 7/1999 | Visscher et al. | 604/387 |
| 6,004,306 A | 12/1999 | Robles et al. | |
| 6,107,537 A | 8/2000 | Elder et al. | |
| 6,120,487 A | 9/2000 | Ashton | |
| 6,198,019 B1 * | 3/2001 | Hansson et al. | 604/378 |
| 6,231,554 B1 * | 5/2001 | Menard | 604/385.01 |
| 6,254,584 B1 * | 7/2001 | Osborn et al. | 604/385.17 |
| 6,306,123 B1 * | 10/2001 | Salerno et al. | 604/385.31 |
| 6,328,724 B1 * | 12/2001 | Ronnberg et al. | 604/385.24 |
| 6,432,098 B1 | 8/2002 | Kline et al. | |
| 6,440,113 B1 * | 8/2002 | Brisebois et al. | 604/385.01 |
| 6,503,233 B1 * | 1/2003 | Chen et al. | 604/385.01 |
| 6,520,945 B1 * | 2/2003 | Hansson | 604/385.24 |
| 6,613,955 B1 * | 9/2003 | Lindsay et al. | 604/378 |
| 6,673,982 B1 * | 1/2004 | Chen et al. | 604/378 |
| 6,802,832 B2 * | 10/2004 | Hansson et al. | 604/385.01 |
| 6,867,345 B2 * | 3/2005 | Shimoe et al. | 604/378 |
| 6,953,451 B2 * | 10/2005 | Berba et al. | 604/385.01 |
| 7,145,054 B2 * | 12/2006 | Zander et al. | 604/380 |
| 7,223,900 B1 * | 5/2007 | Lariviere et al. | 604/380 |
| 2001/0007065 A1 * | 7/2001 | Blanchard et al. | 604/369 |
| 2002/0193767 A1 * | 12/2002 | Mavinkurve et al. | 604/385.04 |
| 2003/0093054 A1 * | 5/2003 | Sierri et al. | 604/385.04 |
| 2003/0225385 A1 * | 12/2003 | Glaug et al. | 604/385.01 |
| 2003/0233082 A1 | 12/2003 | Kline et al. | |
| 2004/0204698 A1 | 10/2004 | Zenker et al. | |
| 2005/0197050 A1 * | 9/2005 | Prasad et al. | 451/41 |
| 2006/0276767 A1 * | 12/2006 | Ueminami et al. | 604/385.31 |
| 2007/0244455 A1 * | 10/2007 | Hansson et al. | 604/385.201 |

FOREIGN PATENT DOCUMENTS

| | | |
|---|---|---|
| JP | 05-039691 | 4/1991 |
| JP | H0539691 Y2 * | 8/1993 |
| WO | WO 93/01781 A | 2/1993 |
| WO | WO 9516746 A1 | 6/1995 |
| WO | WO 02/066086 A1 | 8/2002 |

* cited by examiner

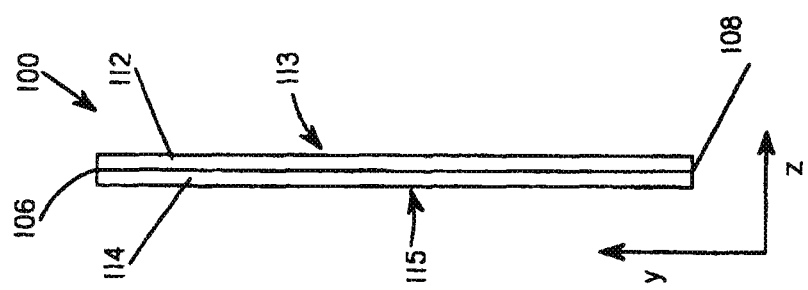
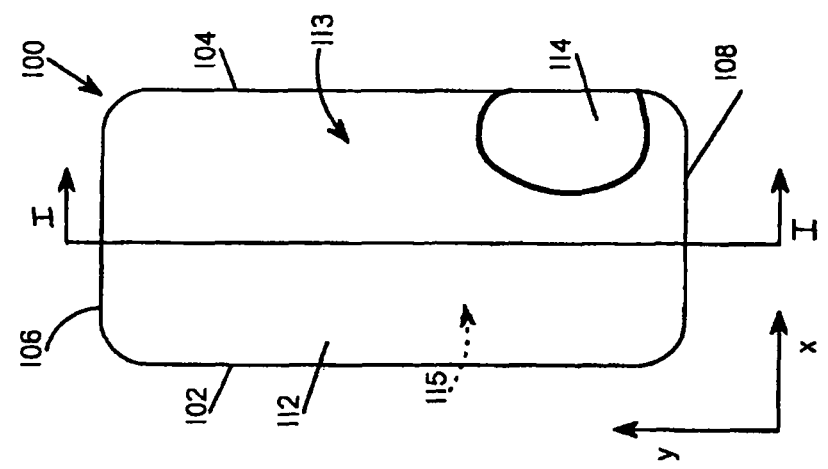
FIG. 1B
FIG. 1A

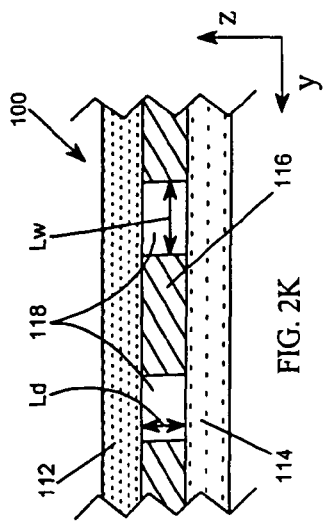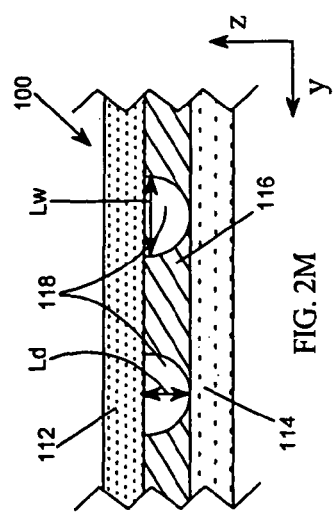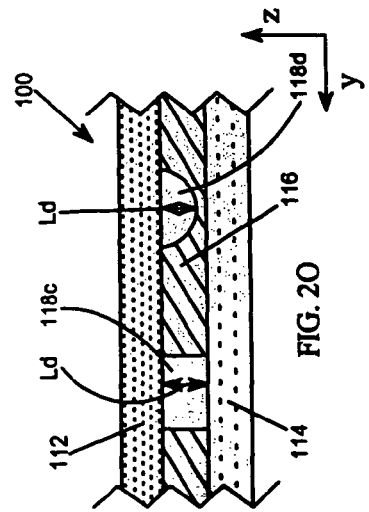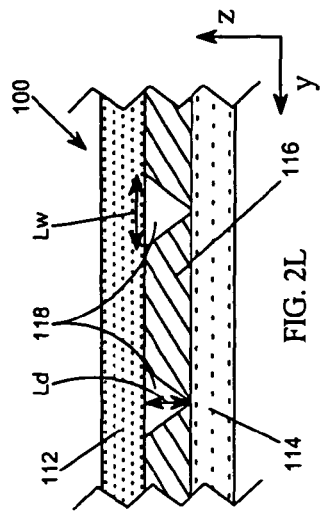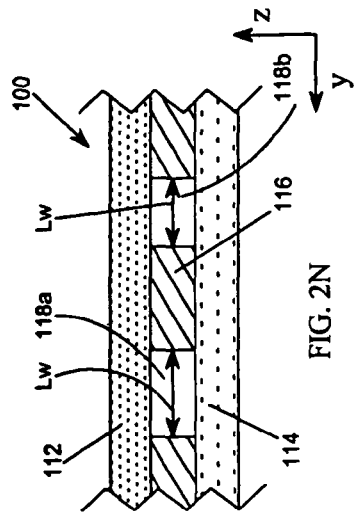

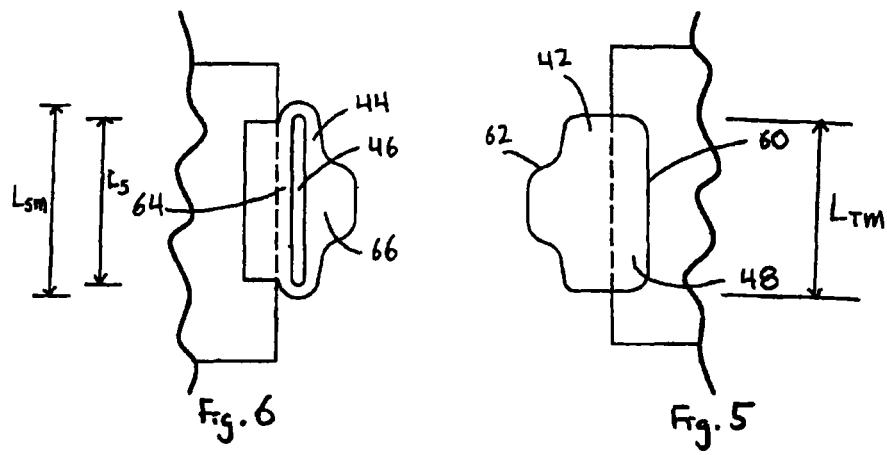
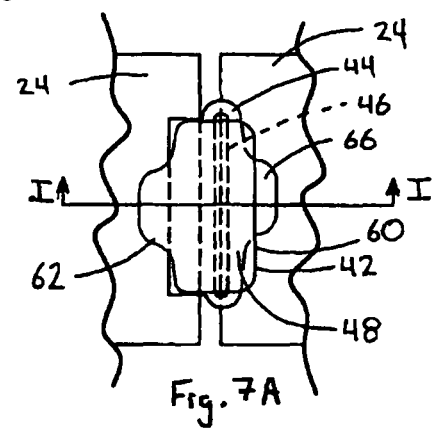
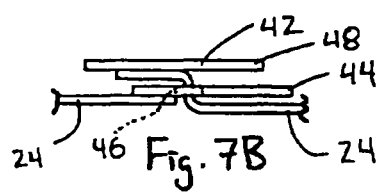

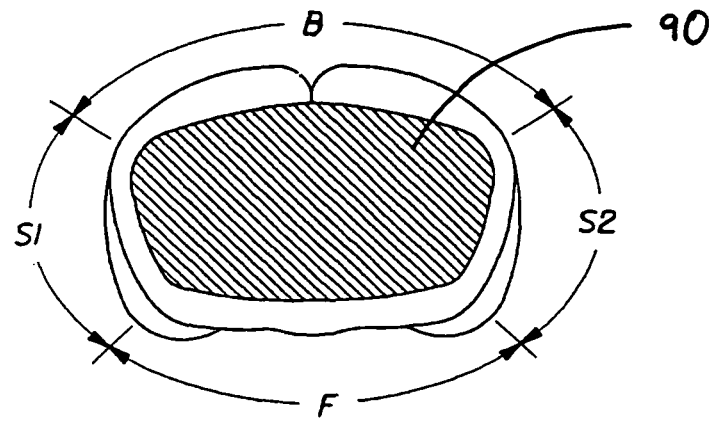
Fig. 8 A
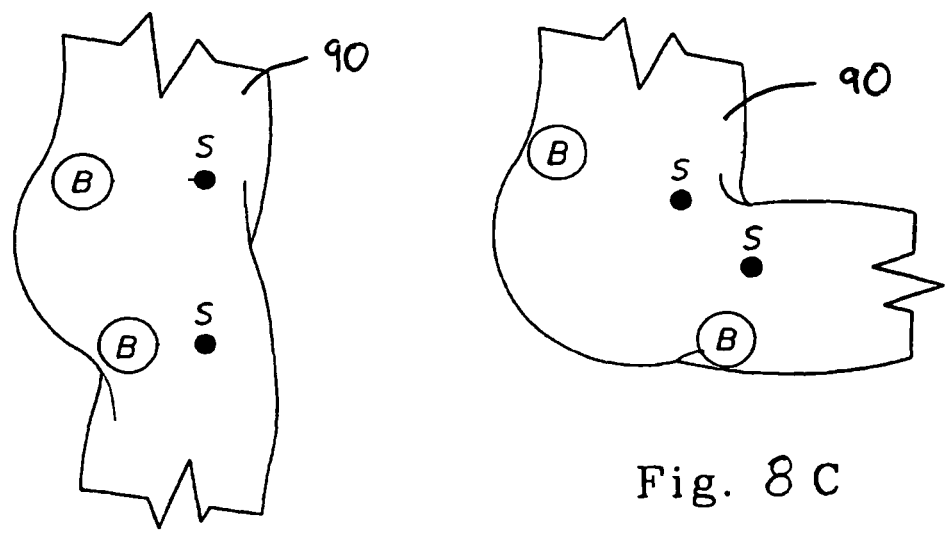
Fig. 8 B
Fig. 8 C

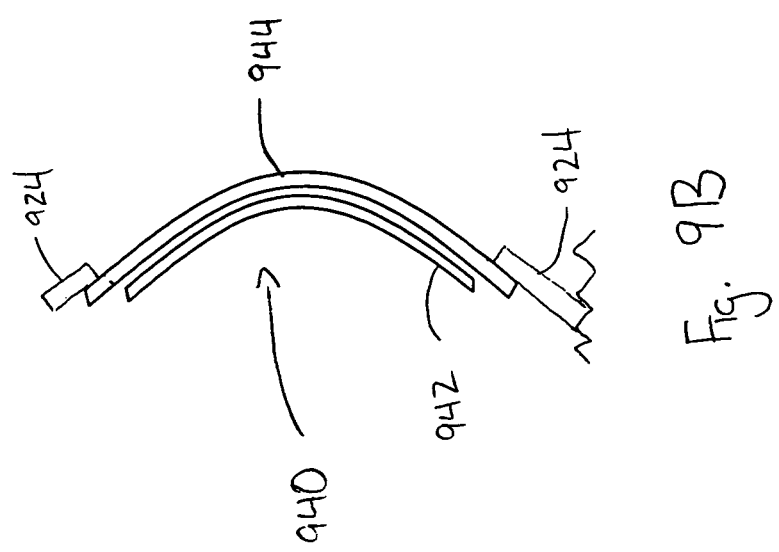

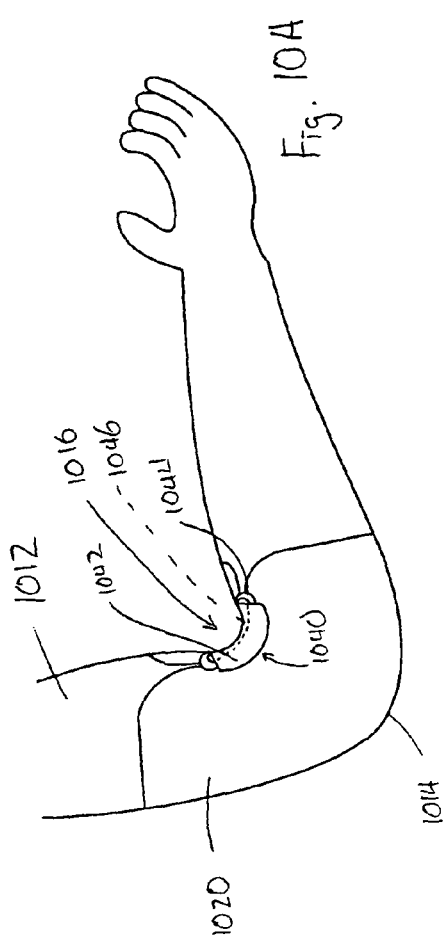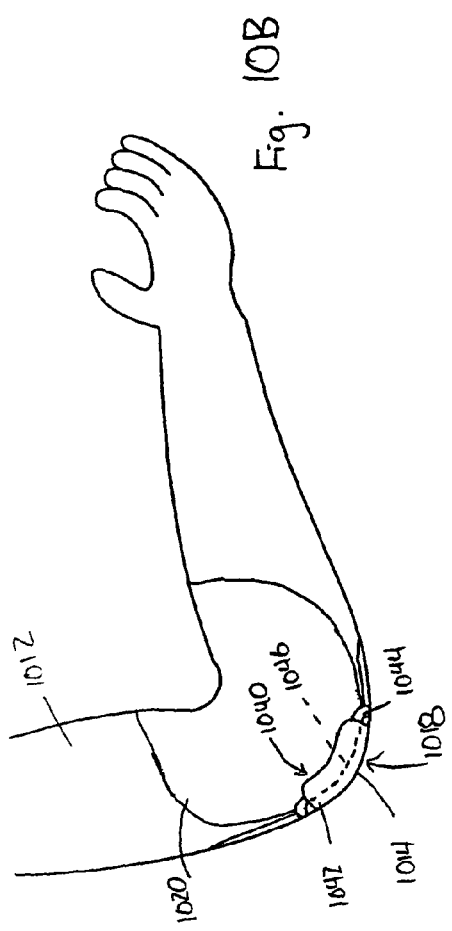

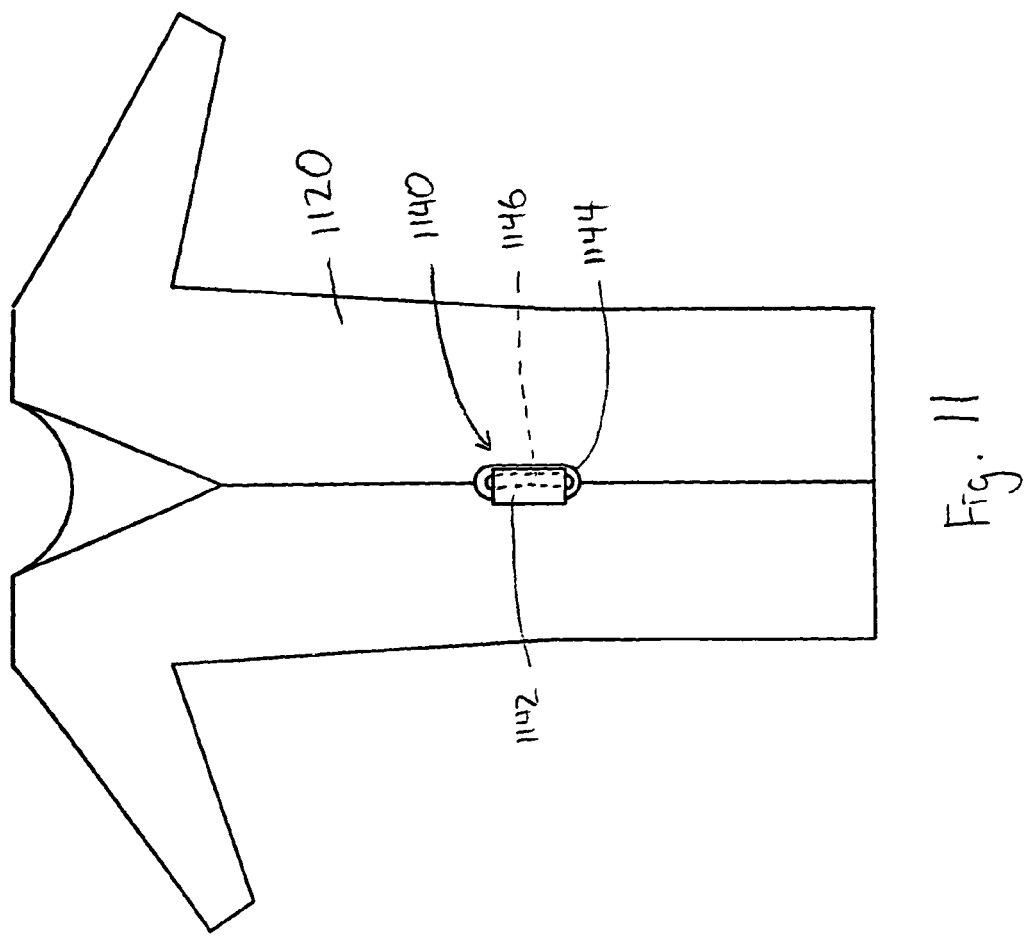

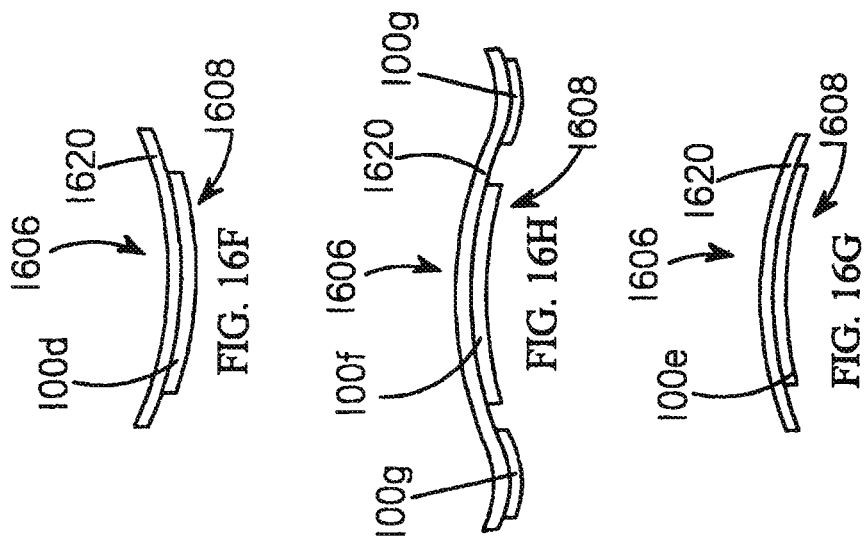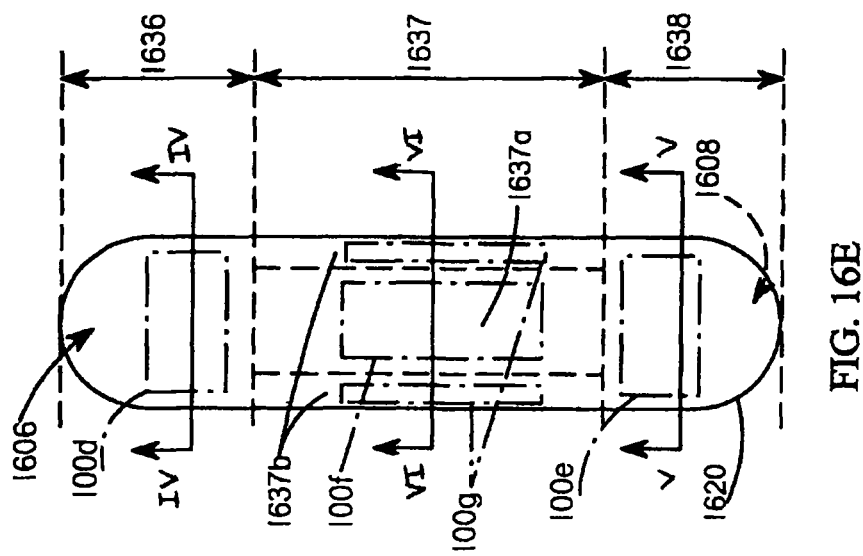

PREFERENTIAL BEND STRUCTURE AND ARTICLES CONTAINING SAID STRUCTURE

FIELD OF INVENTION

This invention relates to a preferential bend structure having a preferential direction of bend that may be used as a fastener, reinforcing structure, or a shaping structure in consumer goods.

BACKGROUND OF THE INVENTION

Many consumer-goods and commercial-goods or components of these goods may be subjected to deforming forces that can result in the bending, folding, buckling, or other deflection of the good or component. Sheet-like structures like fabrics, nonwovens, plastic films, laminates, and the like are particularly susceptible to deflection. Generally, it is desirable that sheet-like structures exhibit some degree of rigidity but excessive rigidity can be problematic.

A fastening system is an example of a component on a commercial good or a consumer good that may require a sheet-like structure that exhibits both rigid and pliant characteristics. While a variety of fastening systems exist (i.e., adhesive, cohesive, mechanical such as hook and loop), a sheet-like structure exhibiting both rigid and pliant characteristics would be particularly beneficial in forming a tab and slot fastener. The tab and slot fastener comprises a substantially planar tab member and a substantially planar slot member having a slot (i.e., slit, aperture) there through. In operating the fastener, the tab member is passed through the slot of the slot member to engage the fastening device. Once passed through the slot, at least a portion of the tab member overlaps the slot member to prevent the tab member from disengaging from the slot member.

The tab and slot member will desirably exhibit some degree of rigidity. For example, an engaged (i.e., fastened) tab and slot fastener may experience a tensioning force where the tab member is pulled in a first direction and the slot member is pulled in a direction opposite of the first direction. With adequate force, the tab member and/or the slot member may deform which can result in unintentional separation of the fastener. For example, the tensioning force may deform the tab member so that it may be pulled back through the slot of the slot member. This unintentional separation of the fastener may be highly undesirable. For instance, the tab and slot fastener may be used in a consumer good such as a diaper to interconnect a front waist section and a rear waist section of the diaper. A tensioning force may be applied to the fastener when the child bends, stretches, or moves. The tensioning force may deform the tab member allowing for unintentional separation of the fastener, which can result in leakage of body exudates. Furthermore, a degree of rigidity in a tab member and/or a slot member may be beneficial for fastening. Without some rigidity, a wearer is required to push or pull a pliant tab member through a pliant slot member. Some wearers, such as infants or the elderly, may lack the necessary dexterity and hand strength to engage that fastener. Also, if the diaper is to be manufactured in a pre-fastened state (i.e., the tab member is inserted in the slot member during manufacture), a non-rigid tab member and/or slot member can cause significant processing complexity.

While the tab and slot members can be made very rigid to prevent deformation, such rigidity is not without drawbacks. For example, a rigid tab and slot fastener used in a diaper may be very uncomfortable for the wearer. A tab and slot fastener that exhibits a degree of rigidity may also resist deformation when subjected to wear forces exerted by the wearer. If the wearer bends or twists, the fastener may remain rigid and may poke or gouge the wearer. It is desirable that the tab and slot fastener exhibit flexibility in order to accommodate and flex with wearer forces.

Absorbent articles are another consumer good that may require a sheet-like structure that exhibits both rigid and pliant characteristics. Absorbent articles typically comprise an absorbent core or pad. Ideally, in some products, the absorbent core will adopt a U-shape while the article is in wear so exudates are contained in the middle of the core. If the core or pad adopts a planar or an inverted U-shape, exudates are prone to flow away from the core and may leak from the absorbent article. Due to packaging constraints, absorbent articles are packaged flat. This prevents the core from being rigidly formed in a U-shape. It would be desirable for the core to comprise a sheet-like structure that will allow the core to adopt a U-shape while in wear while prohibiting the core from becoming inverted (e.g., adopting an inverted U-shape). However, in certain products such as sanitary napkins, it maybe desirable for the core to assume an inverted U-shape. In such an embodiment, it is more preferred to have the core in contact with the wearer.

Furthermore, absorbent articles comprise several gasketing regions, which are areas adjacent to an opening in the article such as a waist opening or a leg opening. The gasketing regions serve to impede exudate leakage from the article. Waist bands, leg cuffs, and other structures within the gasketing regions of the article need to maintain particular orientations to provide maximum gasketing benefit. For example, a leg cuff should ideally fold, bend, or curve inward toward the leg of the wearer in order to provide a tight seal between the cuff and the wearer's leg. In current absorbent article design, the leg cuff is maintained snug against the wearer's leg by using an elastic member under tension. While elastic members typically maintain the cuff in the correct orientation, problems can still occur. For instance, if the cuff is inadvertently inverted during application, the tensioned elastic members may maintain the inverted configuration of the cuff. It would be desirable for the gasketing regions of an absorbent article to comprise a sheet-like structure that may allow for bending or curvature in one direction but will inhibit or prevent bending or curvature in an opposing direction.

In light of the problems highlighted above, it would be advantageous to provide a structure that exhibits less resistance to bend in one direction compared to the resistance to bend in a second direction (which is opposite to the first direction). A structure is needed that deflects a first distance in response to a first force and deflects a second distance in response to a second force, which is of approximately equal magnitude but opposite in direction to the first force, wherein the first distance is greater than the second distance. Such a structure may be useful in a variety of applications such as for use in consumer or commercial goods such as disposable absorbent articles, medical products, and the like. It would be particularly advantageous to provide a fastening system, such as a tab and slot fastener, comprising a structure exhibiting preferential bend. It is desirable that the fastening system be relatively stiff in one direction to aid in application or processing but remain relatively pliant in an opposing direction to improve comfort. It would also be advantageous to provide a structure exhibiting a preferential bend in an absorbent core of an absorbent article to aid in functionality. Furthermore, it would be advantageous to provide a structure exhibiting a preferential bend in a gasketing region of an absorbent article so as to aid in the containment function and comfort of the article.

SUMMARY OF THE INVENTION

The present invention relates to a preferential bend structure that may have a first face and an opposing second face. The preferential bend structure may comprise at least a base layer and an auxiliary layer, wherein a first deforming force applied to the first face results in a first deflection and a second deforming force applied to the second face results in a second deflection which is equal to the first deflection, and wherein the second deforming force is not equal to the first deforming force. The preferential bend structure may be incorporated into a variety of consumer and commercial goods as described herein.

The present invention also relates to a fastening system comprising an engaging member and a receiving member. The engaging member or the receiving member may comprise a preferential bend structure having a first face and an opposing second face. The preferential bend structure may comprise a base layer and an auxiliary layer, wherein a first deforming force applied to the first face results in a first deflection and a second deforming force applied to the second face results in a second deflection which is equal to the first deflection, and wherein the second deforming force is not equal to the first deforming force.

The present invention also relates to a disposable absorbent article having a body-facing surface, a garment-facing surface, and at least a first end region, a second end region, and an intermediate region. At least one of the first end region, second end region, or intermediate region comprises a first preferential bend structure having a first face and an opposing second face. The first preferential bend structure may comprise a base layer and an auxiliary layer, wherein a first deforming force applied to the first face results in a first deflection and a second deforming force applied to the second face results in a second deflection which is equal to the first deflection, and wherein the second deforming force is not equal to the first deforming force.

In one embodiment, a disposable absorbent article has a body-facing surface, a garment-facing surface, and at least a first end region, a second end region, and an intermediate region; wherein at least one of the first end region, second end region, or intermediate region includes a first preferential bend structure having a first face and an opposing second face, the first preferential bend structure including a base layer and an auxiliary layer; wherein the base layer comprises a material having a compressive modulus of $K_{base}$ and a tensile modulus of $T_{base}$; wherein the auxiliary layer comprises a material having a compressive modulus of $K_{aux}$ and a tensile modulus of $T_{aux}$; wherein a sum of $K_{base}$ and $T_{aux}$ relative to a sum of $K_{aux}$ and $T_{base}$ causes the first preferential bend structure to exhibit a preferential bend wherein a first deforming force applied to the first face results in a first deflection and a second deforming force applied to the second face results in a second deflection which is equal to the first deflection, and wherein the second deforming force is not equal to the first deforming force.

In another embodiment, a disposable absorbent article has opposing longitudinal edges and opposing lateral edges, and wherein the disposable absorbent article includes: a topsheet defining a body-facing surface; a backsheet connected with the topsheet, the backsheet defining a garment-facing surface; an absorbent core disposed between the topsheet and the backsheet; a preferential bend structure including a base layer, a second layer, and an auxiliary layer, wherein the second layer is disposed on the base layer and wherein the second layer is disposed between the base layer and the auxiliary layer; wherein the base layer defines a first surface of the preferential bend structure and the second layer defines a second surface of the preferential bend structure, the second surface opposing the first surface, and wherein the auxiliary layer is joined directly with the second surface; wherein the preferential bend structure extends laterally between the opposing longitudinal edges; wherein the second layer comprises a plurality of void regions, each void region having a void opening and defining a void width and a void depth, and wherein the void width varies along the void depth such that a maximum void width is defined at void opening; wherein each void opening is disposed adjacent the second surface and the auxiliary layer with each void extending into the second layer from the second surface toward the base layer; wherein a first deforming force applied to the first surface results in a first deflection and the first deforming force applied to the second surface results in a second deflection; and wherein the first deflection is greater than the second deflection; wherein preferential bend structure is disposed between the absorbent core and the backsheet with the base layer disposed adjacent the backsheet and the auxiliary layer disposed adjacent the absorbent core; and wherein the preferential bend structure bends laterally across an intermediate region to form a U-shape between the opposing longitudinal edges and is adapted to collect body exudates between a wearer's crotch region and the absorbent core.

BRIEF DESCRIPTION OF THE DRAWINGS

FIG. 1A is a plan view of one embodiment of a preferential bend structure shown partly in section, and having a portion of the structure being cut-away to show underlying detail.

FIGS. 1B-C are cross-sectional views of the embodiment of FIG. 1A taken along sectional line I-I.

FIGS. 2K-O are cross-sectional views of preferential bend structures having various void region configurations.

FIG. 5 is a plan view of a tab member.

FIG. 6 is a plan view of a slot member.

FIG. 7A is a plan view of the tab member of FIG. 5 and the slot member of FIG. 6 in a fastened configuration.

FIG. 7B is a cross-sectional view of the tab and slot members of FIG. 7A taken along sectional line I-I.

FIG. 8A is a top down view (i.e., a head-to-toe view) of a wearer bisected at the waist.

FIG. 8B is a side view of a hip of a wearer in a neutral position.

FIG. 8C is a side view of the hip of a wearer of FIG. 8B in a bent position.

FIG. 9B is a cross-sectional view of the fastening system shown in FIG. 9A taken along sectional line I-I.

FIGS. 10A-B are side views of another suitable embodiment utilizing a fastening system including a preferential bend structure.

FIG. 11 is a front view of another suitable embodiment utilizing a fastening system including a preferential bend structure.

FIG. 16E is a plan view of an absorbent pad comprising multiple preferential bend structures.

FIGS. 16F-H are cross-sectional views of the absorbent pad of FIG. 16E taken through sectional lines IV-IV, V-V, and VI-VI, respectively.

DETAILED DESCRIPTION OF THE INVENTION

Figure 1E:
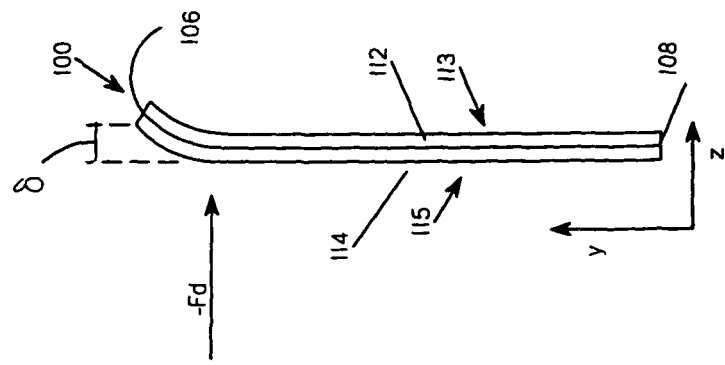
FIGS. 1D-E are cross-sectional views of the embodiment of FIG. 1A showing the deflection resulting from the application of a positive deforming force and a negative deforming force, respectively.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the center of a structure (e.g., the proximal edge of a longitudinally extending element is located nearer to the longitudinal centerline than the distal edge of the same element is located relative to the same longitudinal centerline).

"Body-facing" and "garment-facing" refer to the relative location of an element or a surface of an element or group of elements. "Body-facing" implies the element, face, or surface is nearer to the wearer during wear. "Garment-facing" implies the element, face, or surface is more remote from the wearer during wear (i.e., element or surface is nearer to the wearer's garments that may be worn over the disposable absorbent article).

"Longitudinal," when used in reference to a disposable absorbent article, refers to a direction running substantially perpendicular from a waist edge to an opposing waist edge of the article and generally parallel to longitudinal centerline. Directions within 45 degrees of the longitudinal direction are considered to be "longitudinal"

"Lateral," when used in reference to a disposable absorbent article, refers to a direction running from a longitudinal edge to an opposing longitudinal edge of the article and generally at a right angle to the longitudinal centerline. Directions within 45 degrees of the lateral direction are considered to be "lateral."

"Disposed" refers to an element positioned in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure. A layer or a layered structure that is water-impermeable according to this definition may be permeable to water vapor, i.e., may be "vapor-permeable." As is well known in the art, a common method for measuring the permeability to water, urine, or synthetic urine of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

"Extensibility" and "extensible" mean that the width or length of the component in the relaxed position can be extended or increased.

"Elastic," "elastomer," and "elastomeric" refer to a material which generally is able to extend without breaking or rupturing upon application of a deforming force and is able to recover substantially to its original dimensions after the deforming force has been removed.

"Outboard" and "inboard" refer respectively to the location of an element or region disposed relatively far from or near to the longitudinal or lateral centerline of a structure with respect to a second element. For example, if element A is outboard of element B, then element A is farther from the longitudinal centerline than is element B.

"Pant" refers to disposable absorbent articles having a preformed waist and leg openings. A pant may be donned by inserting a wearer's legs into the leg openings and sliding the pant into position about the wearer's lower torso. Pants are also commonly referred to as "closed diaper," "prefastened diapers," "pull-on diapers," "training pants," and "diaper-pants."

"Deforming Force" refers to a force vector that is in the z-direction. The deforming force may be a component of an applied force (i.e., applied force is a vector sum and the deforming force is one of the constituent vectors).

"Compressive Force" refers to a force vector that is in the x-y plane. The compressive force may be a component of an applied force (i.e., applied force is a vector sum and the compressive force is one of the constituent vectors).

"Preferential Bend" refers to a property where a first deforming force applied to a first planar surface of a structure will result in a first deflection that is greater than a second deflection resulting from a second deforming force applied to a second planar surface of a structure, wherein the second deforming force is of an approximately equal magnitude but in an opposite direction to the first deforming force.

"Layer" when used in reference to a preferential bend structure means a prescribed volume of the structure. Layers may be distinguished by composition, physical characteristics, or geometry.

"Void Region" refers to a region within an intermediate layer devoid of the material which comprises a substantial portion of the intermediate layer.

"Axial Line" refers to a line around which a surface bends.

The present invention is directed to a preferential bend structure and articles incorporating the preferential bend structure. A coordinate system may be used in explaining the preferential bend structure embodiments that follow. The coordinate system used herein includes an x-axis, a y-axis, and a z-axis. The x-axis extends along the surface of the preferential bend structure. The "x-direction" includes (A) all directions that are parallel to and share a common plane with the x-axis and (B) directions within about ±45° from the (A) directions. The y-axis extends along the surface of the preferential bend structure and is generally orthogonal to the x-axis. The "y-direction" includes (A) all directions that are parallel to and share a common plane with the y-axis and (B) directions within about ±45° from the (A) directions. The z-axis is generally orthogonal to both the x-axis and y-axis. The z-axis generally is the axis through which the caliper or thickness of the preferential bend structure is measured. Furthermore, a deforming force that causes the preferential bend structure to bend has at least a partial vector parallel to the z-axis. The "z-direction" includes (A) all directions that are parallel to and share a common plane with the z-axis and (B) directions within about ±45° from the (A) directions. The "x-y plane" is the plane defined by the x-axis and the y-axis as well as all planes parallel thereto.

FIGS. 1A-H depict the preferential bend structure (PBS) 100 with the x, y, and z axes superimposed thereon for reference. FIG. 1A is a plan view of one embodiment of the PBS 100 with a portion of the structure being cut-away to more clearly show the underlying structure. FIG. 1B is a cross-sectional view of the PBS 100 of FIG. 1A taken along sectional line I-I. The PBS 100 may have opposing side edges 102, 104. The PBS 100 may have a first end edge 106 and an opposing second end edge 108. The PBS 100 is shown as having a base layer 112 and an auxiliary layer 114. The base layer 112 and the auxiliary layer 114 may each have a perimeter that may be generally coterminous as shown in FIG. 1A; however, any layer 112 and 114 may be extend past another layer thereby being non-coterminous. The PBS 100 is shown to have a base face 113 and an opposing auxiliary face 115. The base face 113 and the auxiliary face 115 may be substantially planar.

The PBS 100 generally may be a sheet-like structure where the length and width of the structure exceed the thickness of the structure. In certain embodiments, the length and width of the PBS 100 exceed the thickness by several (e.g., >5×) or many times (e.g., >20×).

Figure 1D:
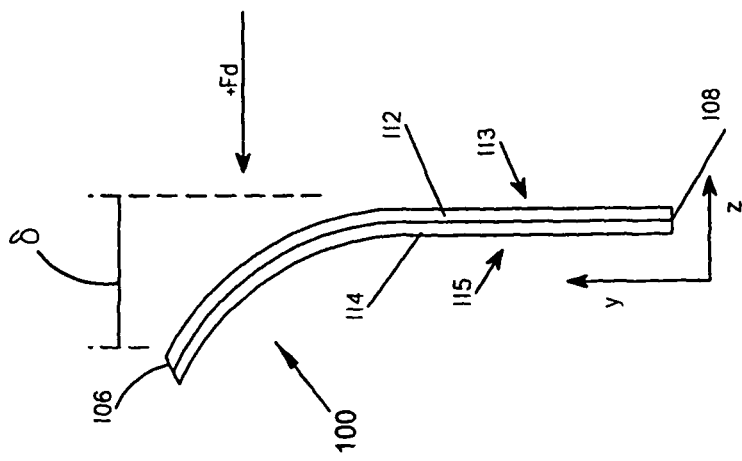
Figure 1C:
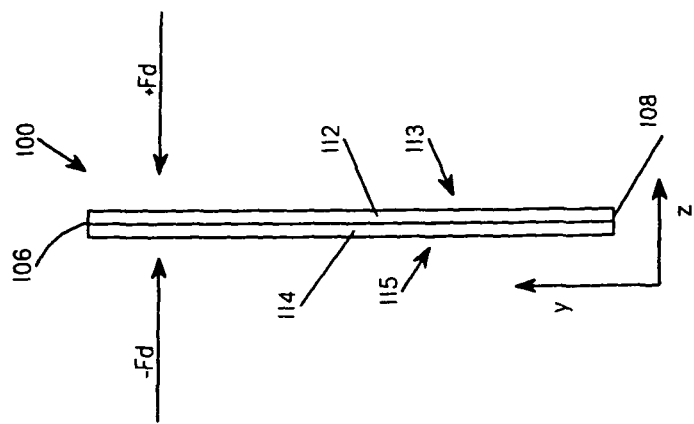

During use as illustrated in FIG. 1C, the PBS 100 may be subjected to a deforming force $F_d$. The deforming force $F_d$ is generally orthogonal to a face of the PBS 100 (e.g., the base face 113 and an opposing auxiliary face 115). The deforming force may be applied from opposite directions, $+F_d$ or $-F_d$ (for purposes of FIGS. 1C-E, $+F_d$ or $-F_d$ should be taken as being approximately equal in magnitude but opposite in direction).

FIG. 1D illustrates a positive deforming force, $+F_d$, being applied to the base face 113 of the PBS 100 proximate to the first edge 106 while the second edge 108 is held stationary. The positive deforming force $+F_d$ may place the base layer 112 in a state of tension and the auxiliary layer 114 in a state of compression. The PBS 100 may exhibit a positive deflection ($+\delta$) from the x-y plane in the direction of and as a result of the positive deforming force $+F_d$. For descriptive purposes, the PBS 100 in FIG. 1D may be referred to as being bent or exhibiting bend toward the auxiliary layer 114.

Alternatively, as shown in FIG. 1E, the negative deforming force $-F_d$ may be applied to auxiliary face 115 of the PBS 100 proximate to the first edge 106 while the second edge 108 is held stationary. The negative deforming force $-F_d$ may place the base layer 112 in a state of compression and the auxiliary layer 114 in a state of tension. In response to the negative deforming force $-F_d$, the PBS 100 may exhibit a negative deflection ($-\delta$) from the x-y plane in the direction of the negative deforming force $-F_d$. For descriptive purposes, the PBS 100 in FIG. 1D may be referred to as being bent or exhibiting bend toward the base layer 112.

FIGS. 1D-E illustrate one aspect of the present invention where the PBS 100 may exhibit a preferential bend evidenced in that, given deforming forces of approximately equal magnitude ($|+F_d|=|-F_d|$), the magnitude of the resultant deflections are not equal ($|+\delta|\neq|-\delta|$). However, in another aspect of the present invention, the PBS 100 may exhibit a preferential bend evidenced in that, given deflections of approximately equal magnitude ($|+\delta|=|-\delta|$), the magnitude of the deforming forces causing said deflections are not equal ($|+F_d|\neq|-F_d|$). In other words, the PBS 100 requires more force to be applied to one face to yield a prescribed deflection than is required to be applied to an opposite face to yield approximately the same magnitude of deflection. Quantification of deflection is measured by the Percent Load Difference which is determined by the Preferential Bend Test as described in the Test Methods section. The Percent Load Difference is a measure of the percent difference between the load required to yield a prescribed deflection in a first direction versus the load required to yield a prescribed deflection in a second direction, which is opposite the first direction. In certain embodiments, the PBS 100 may exhibit a Percent Load Difference greater than about 10%. Alternatively, the Percent Load Difference may be greater than about 25%, about 50%, or about 75%. In certain embodiments, the Percent Load Difference may approach 100%. In certain embodiments, the PBS 100 will exhibit preferential bend at forces less than or equal to 1.5 kilograms force (kgf).

The PBS 100 can be constructed from a variety of suitable materials to provide the preferential bend characteristic described herein. The materials comprising the base layer 112 and the auxiliary layer 114 may be selected based upon the relative compressive modulus and tensile modulus exhibited by the respective materials. While not wishing to be bound by theory, it is believed that the relative compressive strength and/or tensile strength of the materials comprising the base layer 112 and the auxiliary layer 114 may produce the preferential bend characteristic. The deflection of a simple cantilever beam (e.g., homogenous construction) with a first fixed end and a second load end may be calculated according to the equation:

$$\delta = \frac{FL^3}{3EI}$$

wherein $\delta$=deflection, F=force, L=length of the beam, E=elastic modulus which comprises compressive modulus K and tensile modulus T, and I=moment of inertia. However, in a more complex composite system like the PBS 100, deflection is the combination of compression of one layer and extension of another layer. For example, in FIG. 1D, the auxiliary layer 114 is subjected to a compressive load and the base layer 112 is subjected to a tensile load. Conversely, FIG. 1E depicts the auxiliary layer 114 being subjected to a tensile load and the base layer 112 being subjected to a compressive load. Therefore, in a composite system such as the PBS 100, deflection is dependent upon the compressive modulus and the elastic modulus of the constituent layers.

For the following embodiments, the PBS 100 may comprise a base layer 112 and an auxiliary layer 114 wherein: (i) the base layer 112 may comprise a material exhibiting a compressive modulus $K_{base}$ and a tensile modulus $T_{base}$ and (ii) the auxiliary layer 114 may comprise a material exhibiting a compressive modulus $K_{aux}$ and a tensile modulus $T_{aux}$. Without wishing to be bound by theory, it is believed that the direction of preferential bend can be predicted based upon comparing the compressive modulus K and the tensile modulus T of materials comprising the base layer 112 and the auxiliary layer 114 given that the base layer 112 and the auxiliary layer 114 share a common geometry. Likewise, the PBS 100 may be constructed to exhibit a prescribed preferential bend depending upon the selection of materials that constitute the base layer 112 and auxiliary layer 114.

In certain embodiments, the base tensile modulus $T_{base}$ and the auxiliary tensile modulus $T_{aux}$ may be approximately equal. Since the tensile moduli are approximately equal, the preferential bend characteristic is controlled by the relative base compressive modulus $K_{base}$ and the auxiliary compressive modulus $K_{aux}$. The PBS 100 will preferentially bend toward the layer having the lower compressive modulus. For example, if auxiliary compressive modulus is less than the base compressive modulus ($K_{aux}<K_{base}$), the PBS 100 will exhibit greater deflection when bending toward the auxiliary layer 114 for a given force compared the deflection when bending toward the base layer 112.

In other embodiments, the base compressive modulus $K_{base}$ and the auxiliary compressive modulus $K_{aux}$ may be approximately equal. Since the compressive moduli are approximately equal, the preferential bend characteristic is controlled by the relative base tensile modulus $T_{base}$ and auxiliary tensile modulus $T_{aux}$. The PBS 100 will preferentially bend toward the layer having the higher tensile modulus. For example, if auxiliary tensile modulus is greater than the base tensile modulus ($T_{aux}>T_{base}$), the PBS 100 will exhibit greater deflection when bending toward the auxiliary layer 114 for a given force compared the deflection when bending toward the base layer 112.

In other embodiments, neither the compressive moduli (K) of the base layer 112 and auxiliary layer 114 nor the tensile moduli (T) of the base layer 112 and auxiliary layer 114 are approximately equal. The direction of the preferential bend of the PBS 100 may be determined based upon the sum of the base compressive modulus $K_{base}$ and the auxiliary tensile modulus $T_{aux}$ (i.e., $K_{base}+T_{aux}$) compared to the sum of the auxiliary compressive modulus $K_{aux}$ and the base tensile modulus $T_{base}$ (i.e., $K_{aux}+T_{base}$). For example, if the sum of the base compressive modulus and the auxiliary tensile modulus is greater than the sum of the auxiliary compressive modulus and the base tensile modulus ($K_{base}+T_{aux}>K_{aux}+T_{base}$), the PBS 100 may exhibit a preferential bend toward to auxiliary layer 114. Conversely, if the sum of the base compressive modulus and the auxiliary tensile modulus is less than the sum of the auxiliary compressive modulus and the base tensile modulus ($K_{base}+T_{aux}<K_{aux}+T_{base}$), the PBS 100 may exhibit a preferential bend toward to base layer 112.

In other embodiments, the sum of the base compressive modulus $K_{base}$ and the auxiliary tensile modulus $T_{aux}$ may be approximately equal to the sum of the auxiliary compressive modulus $K_{aux}$ and the base tensile modulus $T_{base}$ (i.e., $K_{base}+T_{aux} \approx K_{aux}+T_{base}$). For this embodiment, the structure may exhibit no readily discernable preferential bend.

Figure 1F:
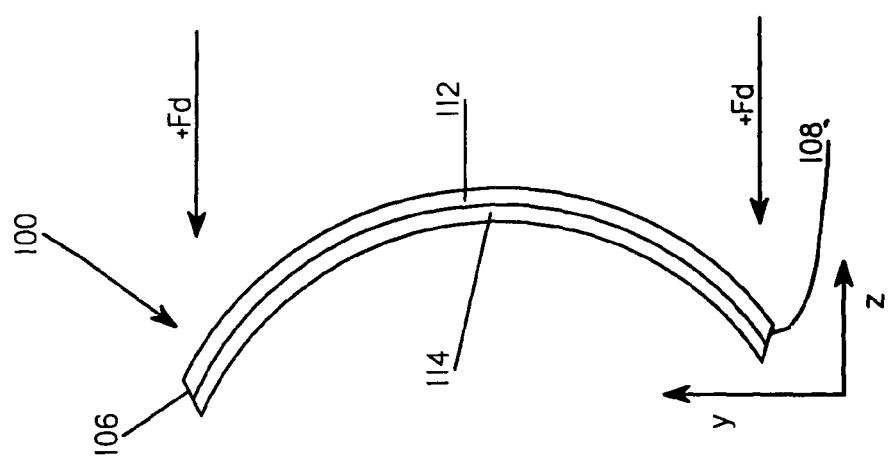
FIG. 1F is a cross-sectional view of the embodiment of FIG. 1A showing the deflection resulting from application of a deforming force on opposite ends of the preferential bend structure.

While FIGS. 1D-E depict the PBS 100 being deformed by a force applied to the PBS 100 proximate to the first edge 106 while the second edge 108 remains held stationary, FIG. 1F depicts the PBS 100 being deformed by a deforming force applied to the first edge 106 and the second edge 108 while the middle of the PBS 100 is held stationary. This embodiment reflects the action that may occur when an applied force comprises a compressive force and a deforming force. Generally, the first edge 106 and the second edge 108 of the PBS 100 are bent out of the x-y plane. While not wishing to be bound by theory, it is believed that the mechanical theory provided above (in reference to FIGS. 1D-E) is equally applicable to the mechanics of FIG. 1F.

The PBS 100 may be formed from a variety of materials and in a variety of physical configurations. FIGS. 1A-F illustrate a PBS 100 having the base layer 112 and the auxiliary layer 114 being substantially similar in their physical configuration. Both layers 112, 114 are shown being sheet-like structures where the width and length of the layer are many times greater than the thickness. The preferential bend characteristics of the PBS 100 may be dependent upon the materials that make up the base layer 112 and the auxiliary layer 114.

The base layer 112 and auxiliary layer 114 may comprise one or more materials having a suitable compressive modulus (K) and tensile modulus (T) to yield the preferential bend characteristic. Suitable materials include but are not limited to, polymeric materials, films, foams, nonwoven webs, woven webs, cellulosic materials, metals, laminates thereof, and combinations thereof. Suitable polymeric materials include but are not limited to polyolefins such as polyethylene and polypropylene, polyesters such as polyethylene terephthalate, polyamides such as nylon, polyacetals, polyvinyl chloride, and styrenic-based polymers. It should be recognized that suitable polymeric materials include homopolymers and copolymers derived from the aforementioned list and saturated, partially saturated, and unsaturated variants thereof. Suitable cellulosic materials include paper, fiberboard, cardboard, paperboard, and the like. The base layer 112 or auxiliary layer 114 may comprise a laminate. For example, either layer 112, 114 may comprise a sheet of polymeric material and a woven or nonwoven substrate. Use of a woven or nonwoven substrate is desirable to impart a degree of softness to the base layer 112 or auxiliary layer 114.

The auxiliary layer 114 and the base layer 112 may be interconnected by in a variety of ways. The layers 112, 114 may be joined by any bonding technique know in the art including heat bonds, pressure bonds, ultrasonic bonds, dynamic mechanical bonds, adhesive bonds, and the like. A particularly suitable adhesive is marketed by Bostik Findley, Inc., Wauwatosa, Wis., as Findley Adhesive 581. Interconnection of the layers 112, 114 may be continuous or discontinuous.

In other suitable embodiments of the PBS 100, the base layer 112 and the auxiliary layer 114 may differ in their physical configuration. Just as the materials that constitute the base layer 112 and the auxiliary layer 114 may be chosen to yield the PBS 100, the physical configuration or geometry of the base layer 112 and the auxiliary layer 114 may be altered so as to yield the PBS 100. FIG. 1G illustrates a cross-sectional view of the PBS 100 with the base layer 112 and the auxiliary layer 114 having differing geometries. The base layer 112 may comprise a one or more discontinuities 117, which are separations in the base layer 112 that may generally extend through the thickness of the PBS 100 from the base face 113 to some point between the auxiliary face 115 and the base face 113. When the base layer 112 is subjected to tension, the discontinuities 117 may act as pivot points. The discontinuities 117 may serve to reduce the tensile modulus of the base layer 112 which may result in the preferential bend characteristic of the PBS 100. The base layer 112 and the auxiliary layer 114 may comprise the same material or may comprise different materials. When the layers 112, 114 comprise the same material, the demarcation between the layers may not be as readily apparent as when the layers comprise differing materials. The demarcation in some embodiments may represent a zone of transition between the base layer 112 and the auxiliary layer 114. The demarcation between the layers 112, 114 should be drawn so as to preserve the physical, geometric, or compositional distinctions of the layers. FIG. 1G shows the demarcation 130 between the base layer 112 with the discontinuities 117 and the continuous auxiliary layer 114. It should be recognized that a PBS 100 can be constructed with discontinuities 117 in the base layer 112 and/or the auxiliary layer 114.

Figure 1H:
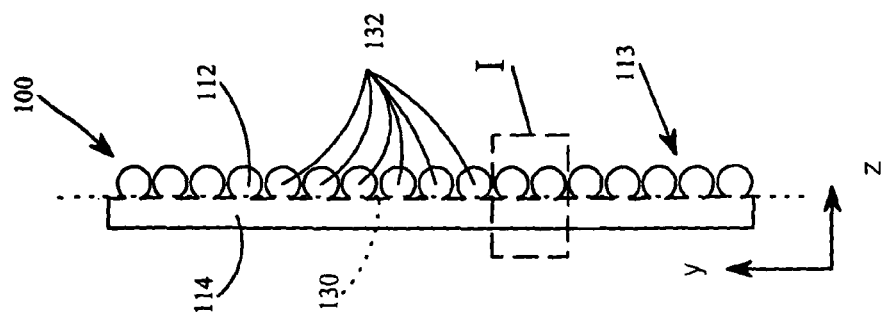
FIGS. 1G-H are cross-sectional views of suitable embodiments of the preferential bend structure.
Figure 1G:
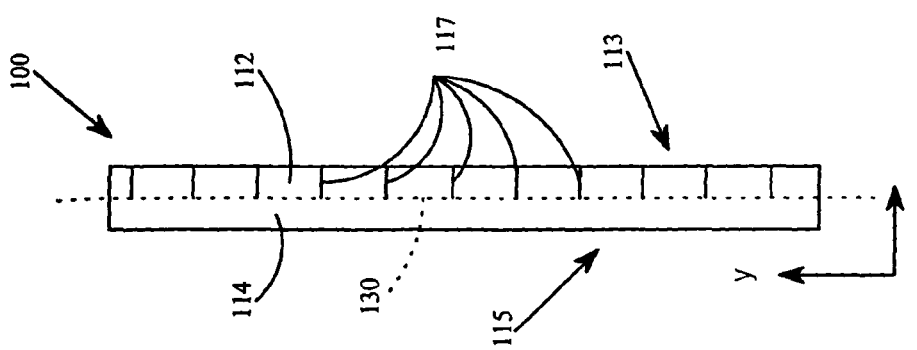
Figure 1I:
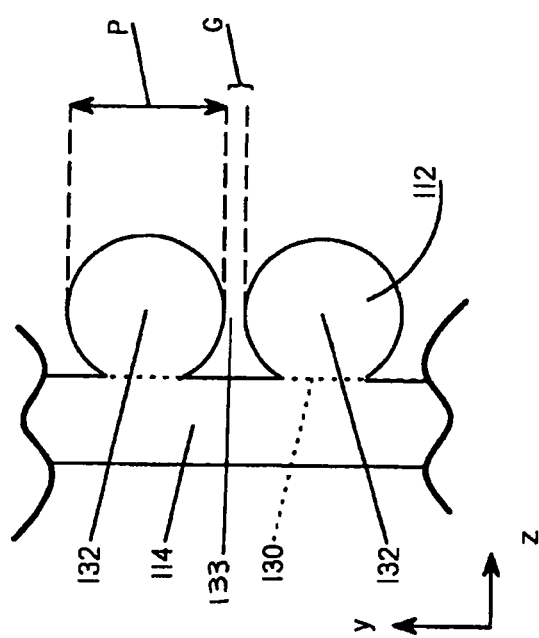
FIG. 1I is a magnified view of the boxed portion I as shown in the preferential bend structure of FIG. 1H

FIG. 1H depicts a cross-sectional view of another suitable embodiment of the PBS 100 wherein the base layer 112 and the auxiliary layer 114 have differing geometries. In this embodiment, the base layer 112 comprises a plurality of protrusions 132 extending from auxiliary layer 114. The protrusions 132 extend to form the base face 113. In this embodiments, the protrusions 132 are substantially spherical in shape; however, the protrusions may be of any three dimensional shape (e.g., conic, cylinder, polyhedron, pyramid, disc, ellipsoid, torus, and the like). The base layer 112 and the auxiliary layer 114 may comprise the same material or may comprise different materials. As with the embodiment in FIG. 1G, the demarcation between the layers 112, 114 should be drawn so as to preserve the physical, geometric, or compositional distinctions of the layers. FIG. 1H shows the demarcation 130 between the base layer 112 comprising the protrusions 132 and the sheet-like auxiliary layer 114. It should be recognized that a PBS 100 can be constructed wherein the base layer 112 and/or the auxiliary layer 114 exhibit protrusions.

FIG. 11 is a magnified view of the boxed portion I as shown in the PBS 100 of FIG. 1H. The protrusions 132 may have a protrusion width P. The plurality of protrusions 132 may have the same protrusion width P or the protrusions may vary in protrusion width P. The protrusions 132 may have a gap 133 between the protrusions 132. The gap 133 has a gap width G. The gap width G between the protrusions 132 may be about equal or may vary. In certain embodiments, the gap width G may be a prescribed percentage of the protrusion width P. For example, the gap width G may be less than about 20% of the protrusion width $$P\left(\frac{G}{P} \cdot 100 < 20\%\right).$$

In alternative embodiments, the gap width G may be less than about 10% or 5% of the protrusion width P. In other embodiments, the gap width may be zero.

While FIG. 1H illustrates one suitable embodiment, it should be readily appreciated that other geometric differentiations can exist between the base layer 112 and the auxiliary layer 114. For example, the layers 112, 114 may take other forms such as films, foils, fabrics, webs, ropes, threads, wires, bands, scrims, and the like. In other embodiments, there may be no clear and distinct demarcation between the base layer 112 and the auxiliary layer 114. The compressive modulus and/or tensile modulus may vary gradually from the base face 113 to the auxiliary face 115. The gradient in properties may be substantially continuous or may occur in a series of steps from the base face 113 to the auxiliary face 115.

Figure 2B:
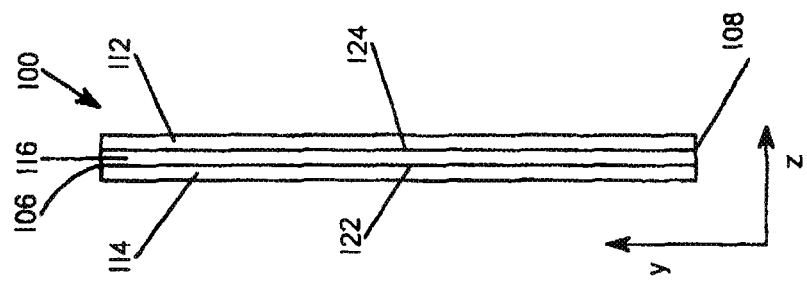
FIG. 2B is a cross-sectional view of the embodiment of FIG. 2A taken along sectional line I-I.
Figure 2A:
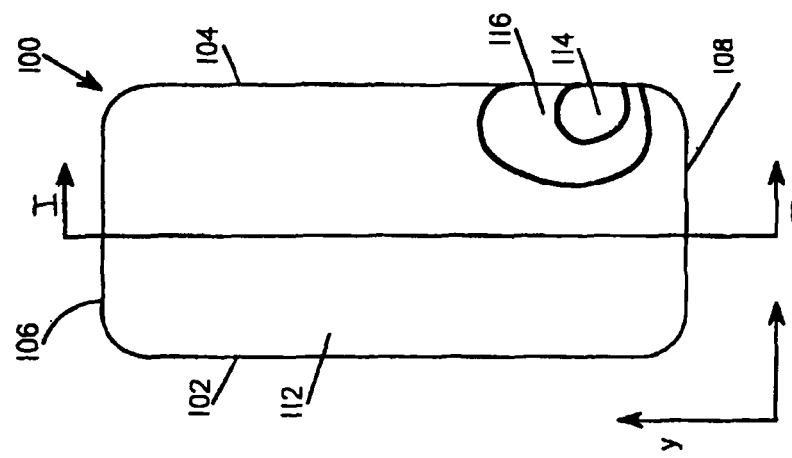
FIG. 2A is a plan view of one embodiment of a preferential bend structure shown partly in section, and having a portion of the structure being cut-away to show underlying detail.

In other suitable embodiments, the PBS 100 may include one or more layers in addition to the base layer 112 and the auxiliary layer 114. FIG. 2A is a plan view of a PBS 100 with portions of the structure being cut-away to more clearly show the underlying structure. FIG. 2B is a cross-sectional view of the PBS 100 of FIG. 2A taken along sectional line I-I. The PBS 100 may comprise the base layer 112, the auxiliary layer 114, and an intermediate layer 116 disposed in between the base layer 112 and the auxiliary layer 114. The intermediate layer 116 may have an auxiliary surface 122 and a base surface 124. The intermediate layer 116 may be of any size and/or shape and may be made from any suitable material. The width of the intermediate layer 116 is generally larger than its thickness. The intermediate layer 116 may comprise one or more of the materials suitable for use as the base layer 112 or the auxiliary layer 114. Ideally, the material selected for the intermediate layer 116 may be resistant to compression of the thickness (e.g., caliper) of the intermediate layer. The intermediate layer 116 may be formed from the same materials as the base layer 112 and/or the auxiliary layer 114.

In certain embodiments, the intermediate layer 116 may have a thickness greater than that of the base layer 112 and/or the auxiliary layer 114. Returning to the deflection equation provided above, the moment of inertia (I) is dependent upon the cross-sectional shape and thickness of the PBS 100, wherein the thickness is measured in the direction of the applied force. For purposes of the PBS 100 in FIG. 2B, the thickness is measured along the z-axis. In a simplistic model (e.g., rectangular cross-section where the moment of inertia equals thickness cubed×width÷12) where the length and width of the PBS 100 remain unchanged, the thickness greatly impacts the force necessary to cause a prescribed deflection of the PBS 100 since thickness is a cubed variable. Inclusion of the intermediate layer 116 into the PBS 100 results in increased thickness of the PBS 100. While not wishing to be bound by theory, it is believed that the increased thickness of the PBS 100 amplifies the preferential bend characteristic by increasing the moment of inertia in the equation for deflection of a simple cantilever beam as provided above. Therefore, the thickness of the intermediate layer 116 is bound only by the end use requirements of the PBS 100 (i.e., if the PBS 100 is used on an article of clothing the intermediate layer should be sized such that the PBS 100 is not a nuisance to a wearer).

The intermediate layer 116 and the base layer 112 may be interconnected in a variety of ways. In embodiments where the intermediate layer 116 and base layer are discrete members, the layers 112, 116 may be joined by any bonding technique know in the art including heat bonds, pressure bonds, ultrasonic bonds, dynamic mechanical bonds, adhesive bonds, and the like. A particularly suitable adhesive is marketed by Bostik Findley, Inc., Wauwatosa, Wis., as Findley Adhesive 581. In other embodiments, the intermediate layer 116 may be integral to the base layer 112 and may be formed together. For example, the base layer 112 and intermediate layer 116 may be casted, molded, or extruded to yield a unitary structure. It should be recognized that, even though the intermediate layer 116 and the base layer 112 may be formed together, the two layers need not be homogenous. The base layer 112 and intermediate layer 116 may be co-extruded from dissimilar materials. Likewise, the auxiliary layer 114 and the intermediate layer 116 may be interconnected or integral in a similar manner as the interconnection or integration of the intermediate layer 116 and the base layer 112. Interconnection of the respective layers 112, 116, 114 may be continuous or discontinuous.

Figure 2D:
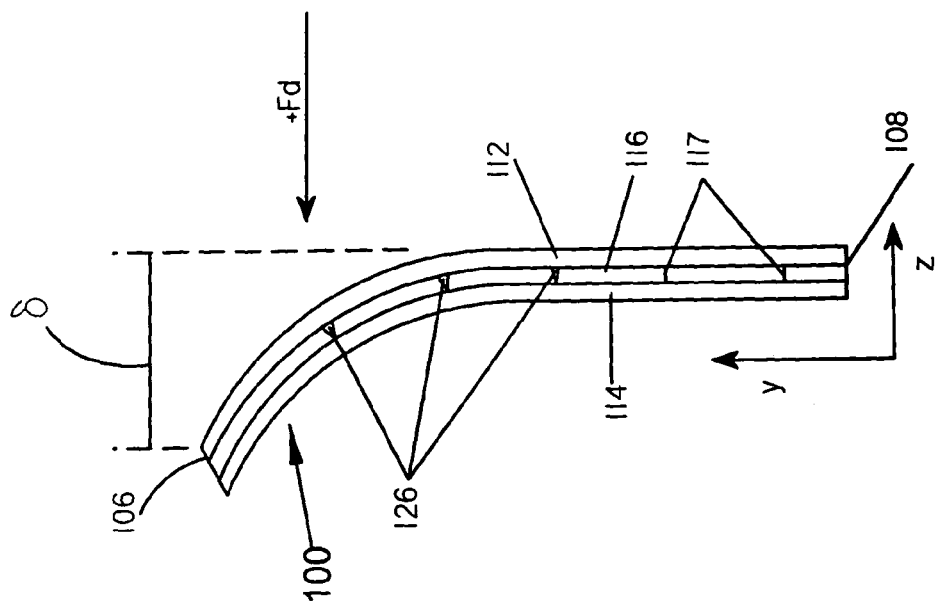
FIG. 2D is a cross-sectional view of the embodiment of FIG. 2C showing the deflection resulting from the application of a positive deforming force.
Figure 2C:
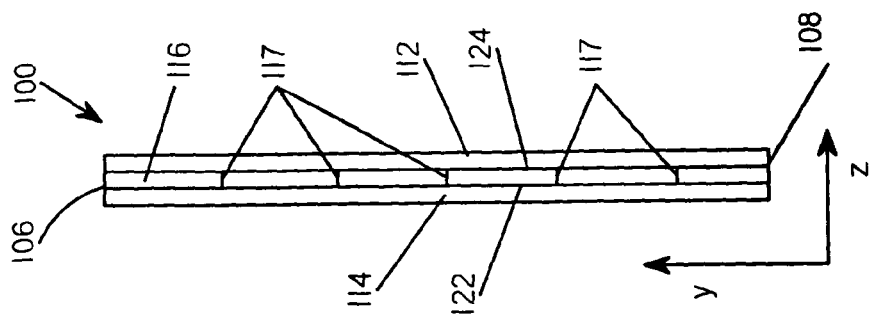
FIG. 2C is a cross-sectional view of one embodiment of a preferential bend structure.

Similar to the two layer embodiments shown in FIGS. 2A-B, the intermediate layer 116 may differ from the base layer 112 and/or the auxiliary layer 114 in physical configuration or geometry. FIG. 2C is a cross-section view of a PBS 100 comprising an intermediate layer 116 with at least one discontinuity 117. Discontinuities 117 are separations in the intermediate layer 116 that extend at least partially through the thickness of the intermediate layer 116. The discontinuities 117 generally may extend from the auxiliary surface 122 to the base surface 124. FIG. 2D is a cross-sectional view of the PBS 100 of FIG. 2C being subjected to a deforming force $+F_d$. The discontinuities 117 may act as pivot points for the PBS 100 forming gaps 126 in the intermediate layer 116. While not wishing to be bound by theory, it is believed that the discontinuities 117 reduce the impact of the tensile modulus of the intermediate layer upon PBS 100. By providing discontinuities 117 in the intermediate layer 116, any tensile strain placed on the intermediate layer 116 is communicated to the discontinuities 117. The intermediate layer 116 effectively becomes a hinge rather than a member under strain. However, absent the deforming force $+F_d$ as illustrated in FIG. 2C the intermediate layer 116 has no gaps 126. As a result, the compressive strength of the intermediate layer 116 (e.g., the compressive modulus K) can add to the overall compressive strength of the PBS 100.

Figure 2F:
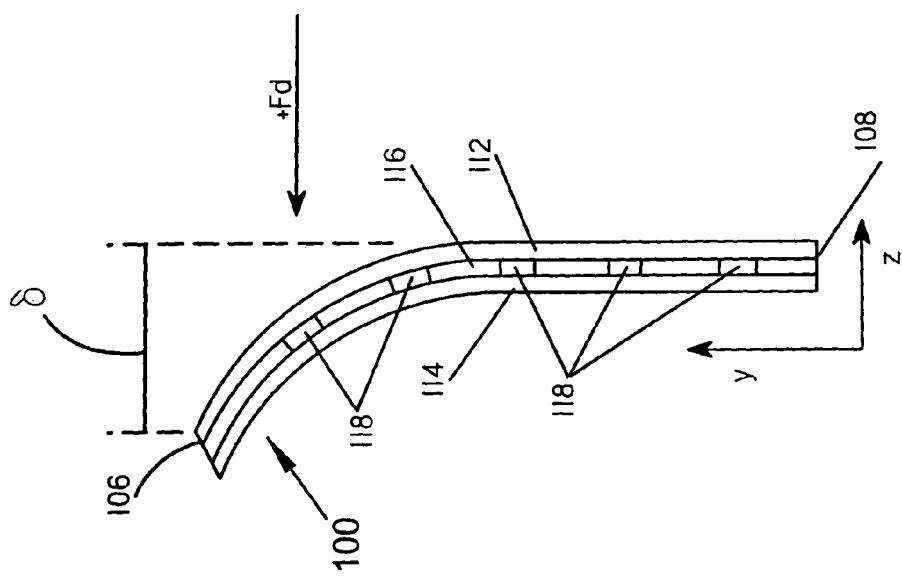
FIG. 2F is a cross-sectional view of the embodiment of FIG. 2E showing the deflection resulting from the application of a positive deforming force.
Figure 2E:
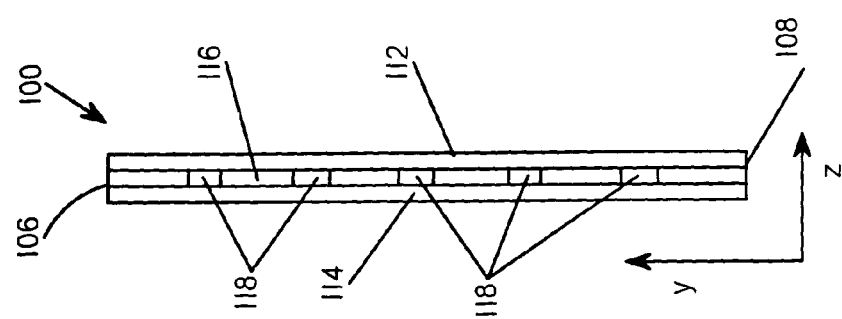
FIG. 2E is a cross-sectional view of one embodiment of a preferential bend structure.

FIG. 2E depicts a cross-sectional view of another suitable embodiment of the PBS 100 wherein the intermediate layer 116 has a physical configuration or geometry different from that of the base layer 112 and/or the auxiliary layer 114. The intermediate layer 116 may include one or more void regions 118 located therein. FIG. 2E shows an embodiment of a PBS 100 having multiple void regions 118 that are present in the absence of a deforming force $F_d$. FIG. 2F shows the PBS 100 of FIG. 2E being subjected to a deforming force $+F_d$. The void region 118 is a region within at least a portion of the intermediate layer 116 that is devoid of the material which forms the intermediate layer 116. The void regions 118 may be filled with a fluid (i.e., gas or liquid) that generally surrounds the PBS 100. Alternatively, the void regions 118 may be filled with a solid material that differs in tensile modulus and/or compressive modulus compared to the material comprising the intermediate layer 116. For example, in one suitable embodiment, the void regions 118 may comprise an open-cell foam while the intermediate layer 116 may comprise polypropylene or polyethylene.

Figure 2H:
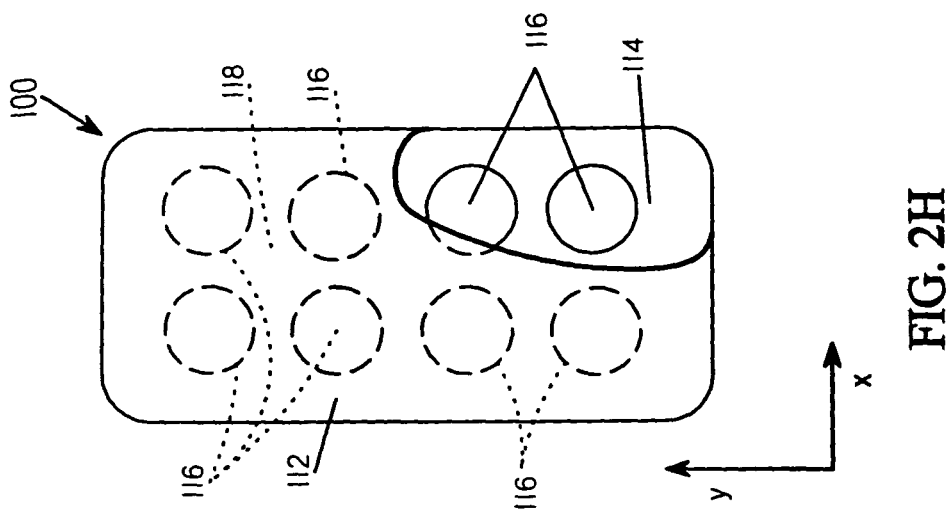
FIGS. 2G-2J are plan views of suitable embodiments of preferential bend structures having various void region configurations, and having a portion of the structure being cut-away.
Figure 2G:
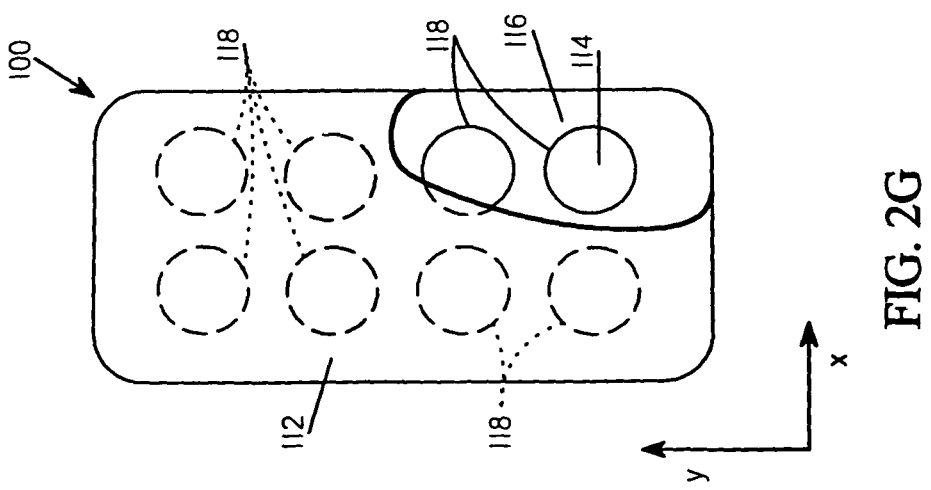

There are a variety of possible intermediate layer 116 and void region 118 configurations. The void regions 118 may extend through the length, width, and/or thickness of the intermediate layer 116. In certain embodiments such as shown in cut-away plan view of FIG. 2G, the void regions 118 may be discrete pockets within the intermediate layer 116. This "islands-in-the-sea" configuration has discrete void regions 118 surrounded by the intermediate layer 116. The void region 118 islands may be of any shape or size. Conversely, shown in cut-away plan view of FIG. 2H, the "island-in-the-sea" configuration can be inverted. As shown in FIG. 2H, islands of the intermediate layer 116 are surrounded by an interconnected void region 118. In other suitable embodiments, the void regions 118 may extend from the auxiliary surface 122 to the base surface 124 and from side edge 102 to side edges 104.

Figure 2J:
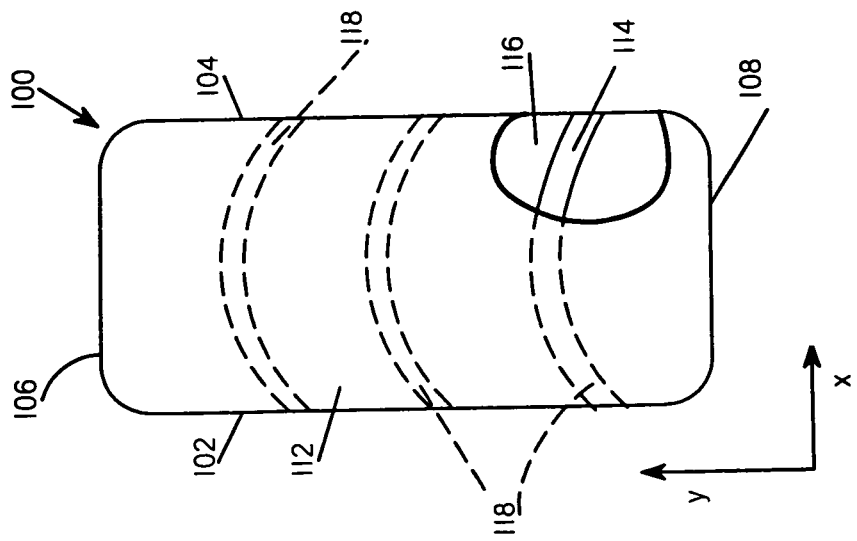
Figure 2I:
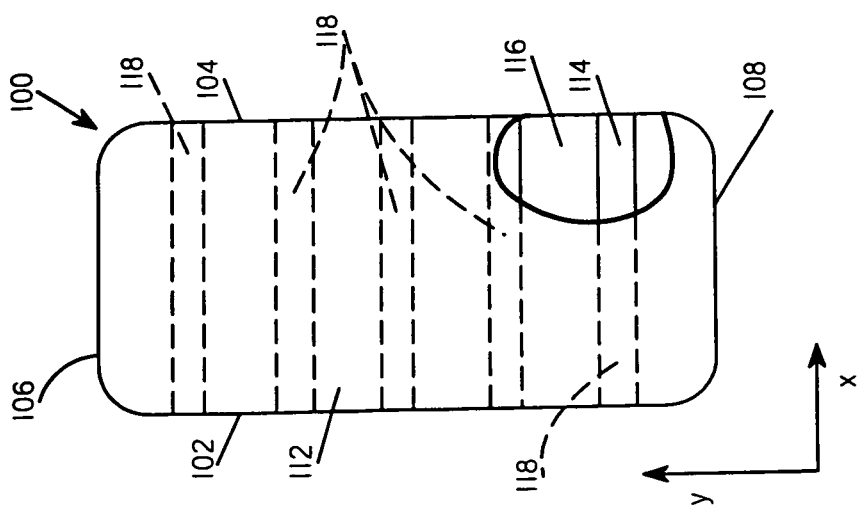

In certain embodiments, such as the embodiment shown in the plan view of FIG. 2I, the void region 118 may extend through the intermediate layer 116 such that a chord (i.e., a straight line segment connecting a point on side edge 102 to a point on side edge 104 of the PBS 100) may be drawn in the x-y plane through the void region 118 such that the chord does not intersect the material that forms the intermediate layer 116. In other embodiments, such as the embodiment shown in the plan view of FIG. 2J, the void region 118 may extend through the intermediate layer 116 such that a curvilinear path (i.e., an unbroken path connecting a point on side edge 102 to a point on side edge 104 of the PBS 100) may be drawn in the x-y plane through the void region such that the path does not intersect the material that formed the intermediate layer 116. Combinations of the two aforementioned embodiments (i.e., chord and curvilinear paths) are likewise feasible.

FIGS. 2K-O show partial cross-sectional views of a variety of void region configurations. The cross-sections are taken approximately orthogonal to the maximum linear dimension of the void region 118. The void region 118 can have a variety of shapes and configurations. The embodiments shown in FIGS. 2K-O are exemplary and nonlimiting. The embodiments are shown having a maximum void depth designated $L_d$ and a maximum void width designated $L_w$. In FIG. 2K, the void regions are shown as being substantially rectilinear. FIG. 2L depicts another substantially rectilinear void region resulting in a "V" shaped void region 118. FIG. 2M depicts the void regions as being partially bound by a curve resulting in a "U" shaped void region 118. The cross-sectional shape of the void regions 118 may be rectilinear, curvilinear, or combination thereof. While FIGS. 2K-M depict void regions 118 have a relatively even void widths $L_w$, it should be recognized that the void regions 118 may have variable void widths $L_w$ within the PBS 100. For example, FIG. 2N illustrates a first void region 118a and a second void region 118b. The void width $L_w$ of the first void region 118a may be greater than the void width $L_w$ of the second void region 118b. It is believed that a PBS 100 having void regions 118a, 118b with differing void widths can result in the PBS 100 displaying variable degrees of curvature when subjected to a deforming force. Likewise, it should be recognized that the void regions 118 may have variable void depths $L_d$ within the PBS 100. FIG. 2O illustrates one such embodiment having a first void region 118c and a second void region 118d. The first void region 118c has a void depth $L_d$ greater than the void depth $L_d$ of the second void region 118d. While this embodiment shows the first void region 118c and the second void region 118d as having differing cross-sectional shapes (i.e., rectilinear and curvilinear), varying void depths can be present in void regions 118 of similar shape. As may be applicable to all embodiments of the void regions 118, the void depth $L_d$ and void width $L_w$ may vary such that $L_d$ may be greater than, equal to, or less than $L_w$. In certain embodiments, it may be desirable that $L_w$ is approximately equal to or greater than $L_d$. It should be readily appreciated that the PBS 100 may have void regions 118 of variable cross-sectional shape, void width, and void depth, and such variants are within the scope of this invention.

Void regions 118 may be formed by a number of techniques. For example, the intermediate layer 116, the base layer 112, and/or the auxiliary layer 114 may each be discrete members. Since the intermediate layer 116 and base layer 112 may need to be joined, the void regions 118 can be formed by spacing the material forming the intermediate layer 116 as it is affixed to the base layer 112. Another technique for forming the void regions 118 involves molten or fluid application of the intermediate layer 116 onto the base layer 112. The material(s) used to form the intermediate layer 116 may be applied in a molten or fluid form to the base layer 112. The molten or fluid material can be applied by an extruder, a print device such as a gravure roll or screen printer, or a coating roll with a take-off mechanism such as a knife, an air-knife, or a metering rod. The molten or fluid material may be applied to result in the intermediate layer 116 and void regions therein 118. The techniques described above are well known and are within the capabilities of a skilled artisan. Likewise, the techniques described in this paragraph for forming the void regions 118 are equally applicable to joining the intermediate layer 116 to the auxiliary layer 114.

Figure 2P:
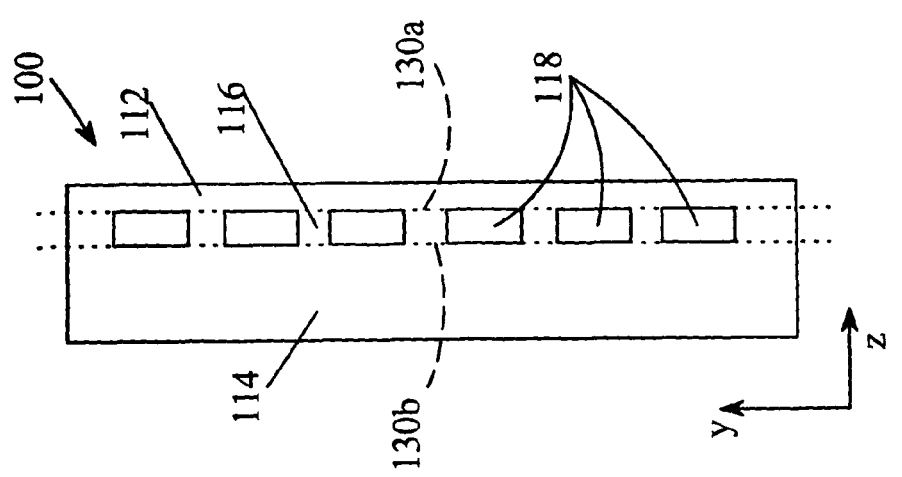
FIG. 2P is a cross-sectional view of a one embodiment of a preferential bend structure.

In certain embodiments, the void regions 118 may be formed as a result integral forming of intermediate layer 116 along with the base layer 112 and/or the auxiliary layer 114. FIG. 2P depicts a PBS 100 wherein the base layer 112, the intermediate layer 116, and the auxiliary layer 114 are integral. The PBS 100 shown in FIG. 2P may be molded with the void regions 118 (e.g., a mold is designed to form the void regions 118 along with the base layer 112, the intermediate layer 116, and the auxiliary layer 114). The demarcation between the layers may not be as readily apparent as when the layers comprise differing materials. The demarcation in some embodiments may represent a zone of transition between the base layer 112, the auxiliary layer 114, and the intermediate layer 116. The demarcation between the layers 112, 114, and 116 should be drawn so as to preserve the physical, geometric, or compositional distinctions of the respective layers. FIG. 2P shows the demarcation 130a between the base layer 112 and the intermediate layer 116 with void regions 118 and the demarcation 130b between the intermediate layer with void regions 118 and the auxiliary layer 114. A suitable embodiment such as the PBS 100, such as shown in FIG. 2P, may be constructed to prompt buckling of at least a portion of the layer while under compression. The PBS 100 of FIG. 2P may be constructed to prompt buckling of at least a portion of the base layer 112 when it is under compression. Buckling may be prompted by forming the base layer 112 from a material having a low compressive modulus and/or by manipulating the void regions 118 so that the base layer 112 has portions with reduced thickness.

In other embodiments, the void regions 118 can be cut, etched, carved, pressed, stamped, or the like into the intermediate layer 116. For example, the intermediate layer 116 can be laser etched to form the void regions 118. For further example, the intermediate layer 116 can be subjected to an embossing roll where projections from the roll can compress and deform the material of the intermediate layer 116 to create the void regions 118.

Figure 3B:
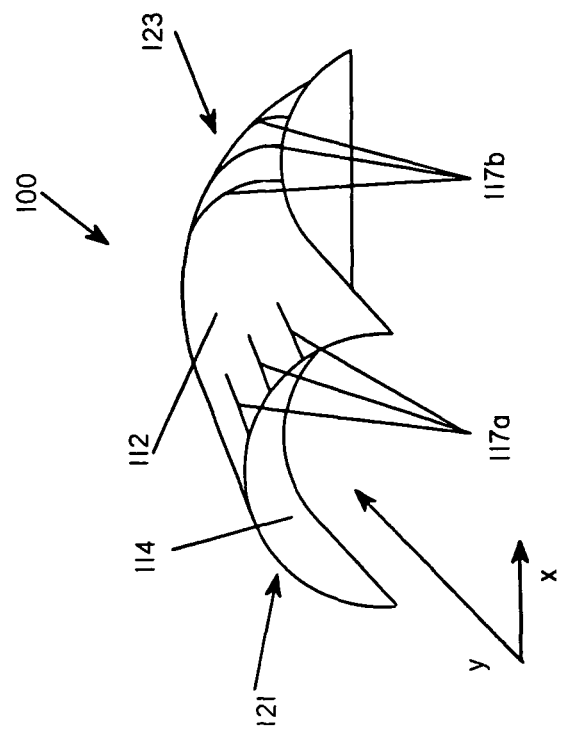
FIGS. 3A-D are embodiments of a preferential bend structure exhibiting bend about more than one axial line.
Figure 3A:
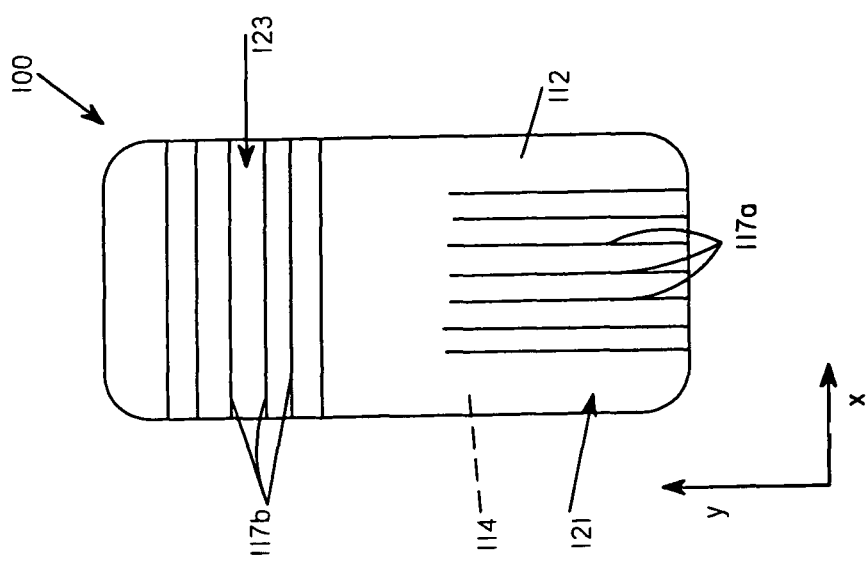

The PBSs 100 exemplified in the various embodiments above may be constructed to exhibit a preferential bend toward the base layer 112 and/or toward the auxiliary layer 114. Furthermore, the embodiments in FIGS. 1D, 1E, 1F, 2D, and 2F depict the PBS 100 bending about axial line that is in the x-direction. However, it should be readily appreciated that a PBS 100 may be constructed that bends about the y-axis or a line in the y-direction. Furthermore, a PBS 100 may be constructed that bends about more than one axial line. For example, FIG. 3A depicts a plan view of a PBS 100 having a first region 121 and a second region 123 wherein the first region 121 bends about one axial line and the second region 123 bends about a different axial line. A PBS 100 exhibiting bend about two different axial lines may be constructed according to the teachings presented above (e.g., a two or more layer structure wherein the preferential bend is created by using differing materials or differing geometries). For example, the PBS 100 of FIG. 3A is constructed similarly to the PBS 100 illustrated in FIG. 1G wherein discontinuities 117 are disposed in the base layer 112. In the embodiment of FIG. 3A, the first region 121 may have linear discontinuities 117a in the base layer 112 extending substantially parallel to the y-axis and the second region 123 may have linear discontinuities 117b in the base layer 112 extending substantially parallel to the x-axis. FIG. 3B is a perspective view of the PBS of FIG. 3A illustrating the two curvatures that may result given a suitable deforming force. The first region 121 may bend about the y-axis and the second region 123 may bend about the x-axis. While the PBS 100 of FIGS. 3A-B illustrate the first region 121 and the second region 123 deflecting in the same z-direction (e.g., both regions 121, 123 are bending toward the auxiliary layer 114), the first region 121 and second region 123 may differ in the direction of preferential bend. For example, the first region 121 may exhibit preferential bend toward the auxiliary layer 114 and the second region 123 may exhibit preferential bend toward the base layer 112.

Figure 3D:
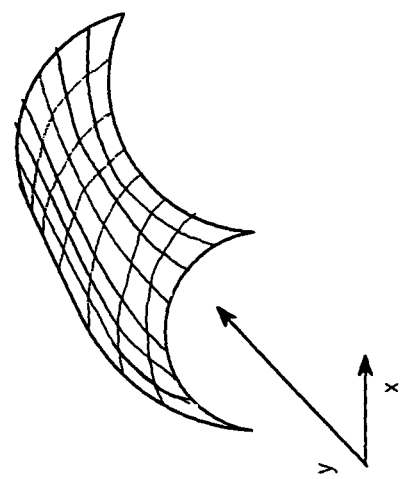
Figure 3C:
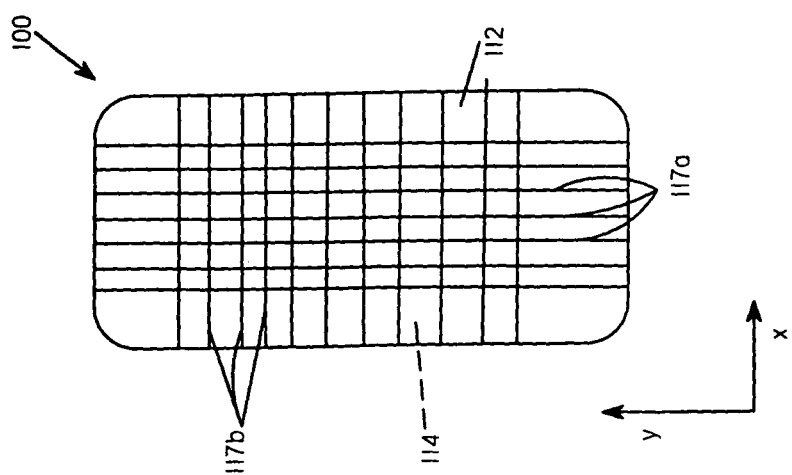

In other embodiments, the PBS 100 may be constructed where a single region exhibits a preferential bend about multiple axial lines. A PBS 100 having a region exhibiting bend about two different axial lines may be constructed according to the teachings presented above (e.g., a two or more layer structure wherein the preferential bend is created by using differing materials or differing geometries). For example, the PBS 100 of FIG. 3C is constructed similarly to the PBS 100 illustrated in FIG. 1G wherein discontinuities 117 are disposed in the base layer 112. In the embodiment of FIG. 3C, the PBS 100 may have linear discontinuities 117a in the base layer 112 extending substantially parallel to the y-axis and may have linear discontinuities 117b in the base layer 112 extending substantially parallel to the x-axis. The linear discontinuities 117a, 117b may intersect. FIG. 3D is a perspective view of the PBS of FIG. 3C illustrating the curvatures about two axial lines that may result given a suitable deforming force. The PBS 100 bends about both the x-axis and the y-axis. The PBS 100 of this execution may take an inverted bowl-like shape given a suitable deforming force. The PBS 100 of FIGS. 3C-D illustrates that the direction of preferential bend about both axial lines is in the same z-direction (e.g., the PBS 100 bends about the x-axis toward the auxiliary layer 114 and the y-axis toward the auxiliary layer 114). However, the PBS 100 may bend about one axial line in a first direction (e.g., toward the auxiliary layer 114) and may bend about another axial line in a second direction (e.g., toward the base layer 112).

As will be explored in further detail below, any of the PBSs described above or within the scope of the present invention may be incorporated into a variety of consumer and commercial goods that may benefit from having a structure exhibiting a preferential direction of bend. In any of the embodiments described herein, the PBS 100 may be a separate element added to the commercial good or fastener. For example, the PBS 100 may be a discrete structure attached to any component (e.g., a topsheet, an absorbent core, a backsheet, a fastening system, a cuff, etc.) of an absorbent article or other commercial good (e.g., a wrap, a medical product, etc.). Alternatively, the PBS 100 may be constructed as part or all of any component of the commercial good or fastener. For example, the PBS 100 may be constructed as part or all of any component (e.g., a topsheet, an absorbent core, a backsheet, a fastening system, a cuff, etc.) of an absorbent article or other commercial good (e.g., a wrap, a medical product, etc.). Further, PBS 100 may be disposed in any suitable location on or in the commercial good or fastener. For example, PBS 100 may be disposed on a body-facing surface of, a garment-facing surface of, or contained within the commercial good or fastener.

Figure 4A:
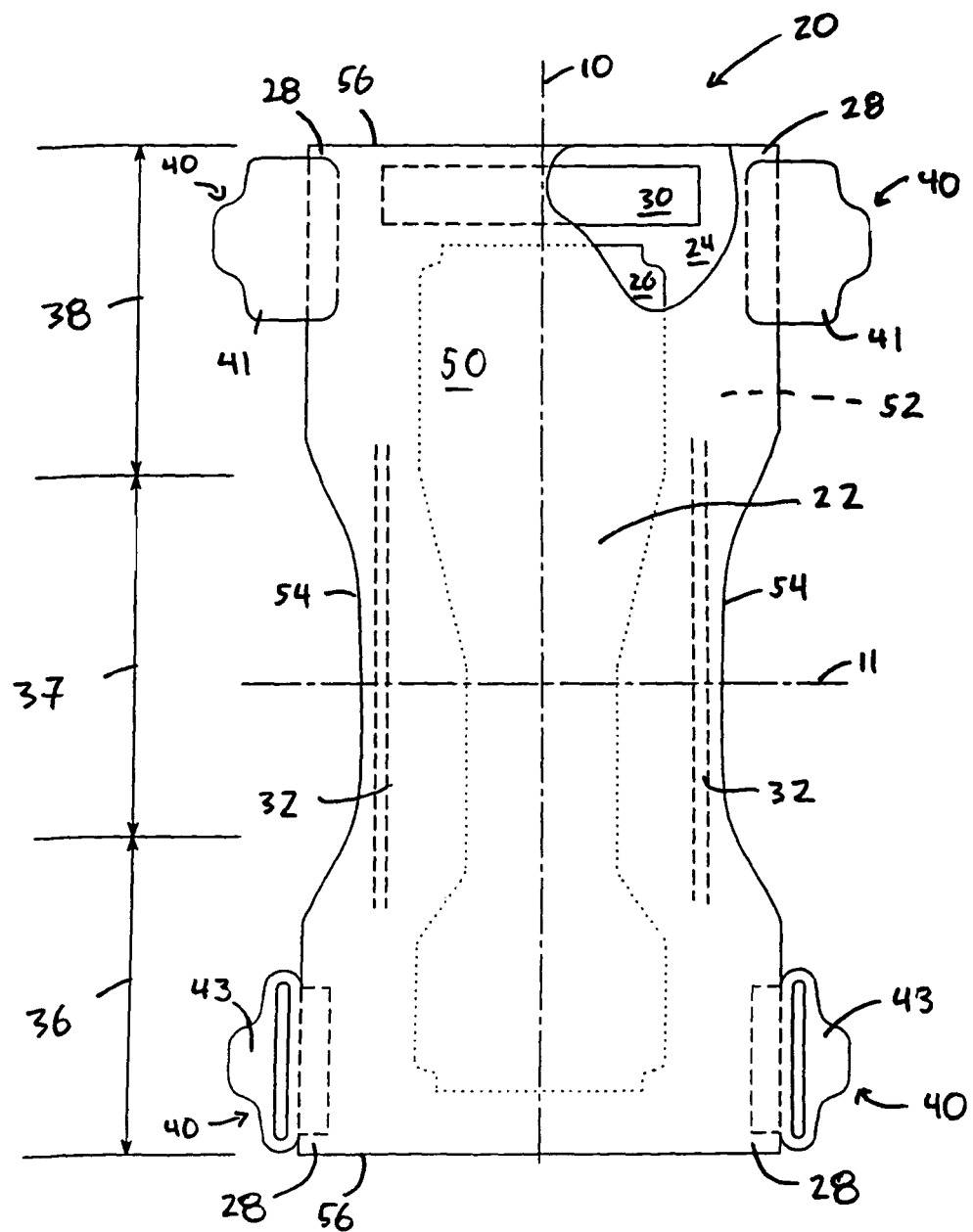
FIG. 4A is a plan view of a suitable absorbent article in a flat, unfastened configuration shown partly in section, and having a portion of the structure being cut-away to show underlying detail.

FIG. 4A is a plan view of one suitable embodiment of a diaper 20 including the fastening system 40 of the present invention in its flat-out, uncontracted state (i.e., with elastic induced contraction pulled out) with portions of the structure being cut-away to more clearly show the construction of the diaper 20. The portion of the diaper 20 which faces or contacts the wearer, the body-facing surface 50, is oriented towards the viewer. As shown in FIG. 4A, the diaper 20 may comprise a liquid pervious topsheet 22; a backsheet 24 joined with the topsheet 22; an absorbent core 26 positioned between the topsheet 22 and the backsheet 24; side panels 28, leg cuffs 32; and a waist feature 30.

The diaper 20 is shown to have an garment-facing surface 52, a body-facing surface 50 opposed to the garment-facing surface 52, a first waist region 36, a second waist region 38 opposed to the first waist region 36, a crotch region 37 positioned between the first waist region 36 and the second waist region 38. The diaper 20 also has a longitudinal centerline 10 and a lateral centerline 11. The diaper 20 also has longitudinal edges 54 and lateral edges 56 (i.e., waist edge). The longitudinal edges 54 may be linear or curvilinear, as shown in FIG. 4A, to provide an "hourglass" shape to the diaper 20. The lateral edges 56 may be linear, as shown in FIG. 4A, or may be curvilinear (e.g., a curvilinear lateral edge 56 may be place in the first waist region to improve fit around a wearer's midriff).

The topsheet 22 and the backsheet 24 may have length and width dimensions generally larger than those of the absorbent core 26. The topsheet 22 and the backsheet 24 may extend beyond the edges of the absorbent core 26 to thereby form the periphery of the diaper 20. The topsheet 22, the backsheet 26, and the absorbent core 26 may be assembled in a variety of well-known configurations such as those described generally in U.S. Pat. Nos. 3,860,003; 5,151,092; 5,221,274; 5,554,145; 5,569,234; 5,580,411; and 6,004,306.

The topsheet 22 is generally a portion of the diaper 20 that may be positioned at least in partial contact or close proximity to a wearer. Suitable topsheets 22 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 22 is generally supple, soft feeling, and non-irritating to a wearer's skin. Generally, at least a portion of the topsheet 22 is water-permeable, permitting liquid to readily penetrate through the thickness of the topsheet 22. A particularly suitable topsheet 22 is available from BBA Fiberweb, Brentwood, Tenn. as supplier code 055SLPV09U. The topsheet 22 may be partially or fully coated with a lotion as is known in the art. The topsheet 22 may be fully or partially elasticized or may be foreshortened so as to provide a void space between the topsheet 22 and the core 26. Exemplary structures including elasticized or foreshortened topsheets are described in more detail in U.S. Pat. Nos. 4,892,536; 4,990,147; 5,037,416; and 5,269,775.

The absorbent core 26 may comprise a wide variety of liquid-absorbent materials commonly used in disposable diapers and other absorbent articles. Examples of other suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures for use as the absorbent core 26 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The backsheet 24 is generally positioned such that it may be at least a portion of the garment-facing surface 52 of the diaper 20. Backsheet 24 may prevent exudates absorbed and contained in the diaper 20 from soiling articles that may contact the diaper 20, such as bedsheets and undergarments. In certain embodiments, the backsheet 24 is substantially water-impermeable. Suitable backsheet 24 materials include films such as those manufactured by Tredegar Industries Inc. of Terre Haute, Ind. and sold under the trade names X15306, X10962, and X10964. Other suitable backsheet 24 materials may include breathable materials that permit vapors to escape from the diaper 20 while still preventing exudates from passing through the backsheet 24. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537.

Backsheet 24 may also consist of more than one layer. The backsheet 24 may comprise an outer cover and an inner layer. The outer cover may be made of a soft, non-woven material. The inner layer may be made of a substantially water-impermeable film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The diaper 20 may further comprise leg cuffs 32 to improve containment of liquids and other body exudates. Each leg cuff 32 may include several different embodiments for reducing the leakage of body exudates in the leg regions. The leg cuffs cuff 32 may be substantially inelastic or may be elastically extensible to dynamically fit at the wearer's leg. The leg cuffs 32 may be formed by one or more elastic members operatively joined to the topsheet 22, backsheet 24, or any other suitable substrate used in the formation of the diaper 20. The leg cuff 32 may also be referred to as outer leg cuffs, leg bands, side flaps, leg cuffs, elastic cuffs, barrier cuffs, gasketing cuffs, second cuffs, and inner leg cuffs. U.S. Pat. No. 3,860,003 describes a disposable diaper which provides a contractible leg opening having a side flap and one or more elastic members to provide an elasticized leg cuff (i.e., gasketing cuff). U.S. Pat. No. 4,909,803 describes a disposable diaper having "stand-up" elasticized flaps (i.e., barrier cuffs) to improve the containment of the leg regions. U.S. Pat. No. 4,695,278 describes a disposable diaper having dual cuffs including a gasketing cuff and a barrier cuff.

The diaper 20 preferably also includes a waist feature 30 that helps provide improved fit and containment. The waist feature 30 is that portion or zone of the diaper 20 which is intended to elastically expand and contract to dynamically fit the wearer's waist. The elastic waist feature 30 is generally disposed longitudinally between the absorbent core 26 and the lateral edge 56 of the diaper 20. Although disposable diapers are generally constructed so as to have two elastic waist features, one positioned in the first waist region 36 and one positioned in the second waist region 38, diapers can be constructed with a single elastic waist feature 30, as shown. Further, while the elastic waist feature 30 or any of its constituent elements can include a separate element affixed to the diaper 20, the elastic waist feature 30 may be constructed as an extension of other elements of the diaper 20 such as the backsheet 24, the topsheet 22 or both the backsheet 24 and the topsheet 22. Examples of suitable waist features include those described in U.S. Pat. Nos. 4,515,595; 5,151,092; and 5,221,274.

Figure 4B:
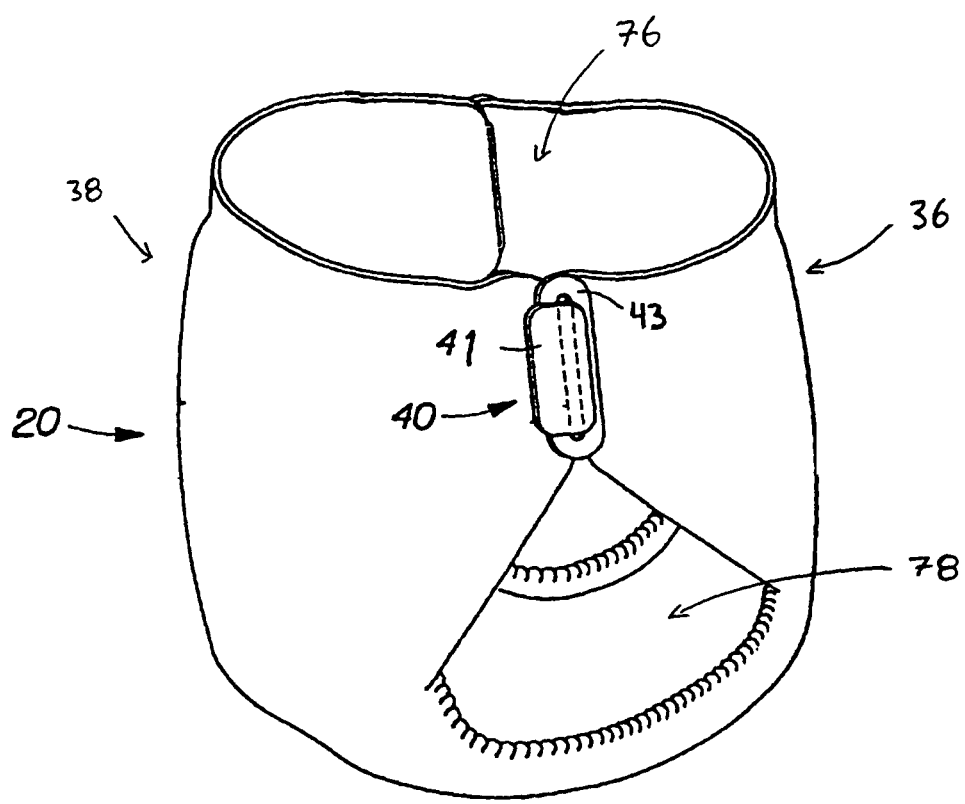
FIG. 4B is a perspective view of the absorbent article of FIG. 4A in a fastened configuration.

The diaper 20 may include a fastening system 40. When fastened, the fastening system 40 interconnects the first waist region 36 and the second waist region 38 which may result in a waist opening 76 and a leg opening 78, as shown in perspective view of diaper 20 provided in FIG. 4B. The fastening system 40 also works with the waist feature(s) 30 to maintain lateral tension in order to keep the diaper 20 in place about the wearer. The fastening system 40 may comprises an engaging member 41 and a receiving member 43. The fastening system 40 generally is capable of joining the first and second waist regions 36 and 38 of the diaper 20 by engaging the engagement member 41 with the receiving member 43. Suitable engagement member 41 and receiving member 43 combinations include: hook/loops, hook/hooks, adhesive/adhesive, adhesive/polymeric film, cohesive/cohesive, button/button hole, tab/slot, and the like. The fastening system 40 may be used alone or in conjunction with other secondary fastening systems which may provide different fastening characteristics from the fastening system 40. For example, a second fastening system may provide a disposal means for fastening the diaper 20 in a configuration convenient for disposal. In another example, a secondary fastening system may provide the diaper 20 with a means for adjusting fit or may increase the strength of the connection between the first waist region 36 and the second waist region 38.

In certain suitable embodiments, the engagement member 41 may be a tab member and the receiving member 43 may be a slot member. FIGS. 5 and 6 are magnified views of the tab member 42 and slot member 44, respectively. The tab member 42 preferably includes a generally elongate member having a proximal edge 60, a distal edge 62, a lip portion 48, and a length $L_{TM}$. The slot member 44 includes an inboard portion 64, an outboard portion 66, and a slot 46 disposed between the inboard portion 64 and the outboard portion 66. The slot member 44 has a length $L_{SM}$ and the slot 46 has a length $L_S$.

In a simple form, the fastening system 40 may be fastened by passing the tab member 42 completely through the slot 46 of the slot member 44. Once the tab member 42 has been passed through the slot member 44, the lip portion 48 of the tab member 42 may be rotated into a plane generally parallel with the plane of the slot member 44 such that at least a part of the lip portion 48 may overlap at least a part of the outboard portion 66 of the slot member 44, as shown in the plan view of FIG. 7A and the cross-sectional view on FIG. 7B taken along sectional line I-I of FIG. 7A. Likewise, the distal edge 62 of the tab member 42 may overlap the inboard portion 64 of the slot member 44. In this configuration, the lip portion 48 of the tab member 42 may prevent the tab member 42 from slipping back through the slot 46 and disengaging the fastening system 40. A portion of the tab member 42 or one or more elements of the diaper 20, such as the backsheet 24, to which the tab member 42 is joined may extend into the slot 46, as shown in FIG. 7B. The material in the slot member 44 may act to resist forces in shear which tend to direct the tab member 42 and the slot member 44 apart.

The tab member 42 may be of any size and/or shape and may be made from any suitable material. In certain embodiments, the tab member 42 may comprise the PBS as described above. Generally, the tab member 42 should be sized to fit through the slot 46 of the slot member 44 with little or no bending or deflection of either component. The shape of the tab member 42 will often be dependent on the end use of the fastening system 40, but in any case should be aesthetically pleasing, easy to hold and maneuver, and capable of maintaining the system 40 in a fastened configuration throughout the intended period of use when subjected to expected forces and external conditions.

The slot member 44 may be of any size and/or shape and may be made from any suitable material. In certain embodiments, the slot member 44 may comprise the PBS 100 as described above. As with the tab member 42, the shape of the slot member 44 and the materials which make up the slot member 44 will be dependent on the end use of the fastening system 40. For example, in end uses such as diapers, the slot member 44 should be designed to be skin friendly (i.e., not harmful to the wearer's skin). It may be desirable to round the edges of the fastening system 40 and to size the slot(s) 46 so as to minimize the likelihood that skin will be caught in the system 40. One way of minimizing the risk is to work the edges of the slot 46 such that they are not sharp. Another way is to make the fastening device more skin friendly include minimizing the thickness of the slot member 44 (preferably less than 0.05 inches) or to design the tab member 42 or slot member such that the slot 46 is filled in when the fastening system 40 is closed. One more way is to provide a soft or compressible material on at least the surface of the fastening system 40 which faces the wearer. Other suitable tab member 42 and slot member 44 configurations are described in U.S. Pat. No. 6,432,098 and U.S. Patent Publication 2003/0233082.

In certain embodiments, both the tab member 42 and the slot member 44 may comprise the PBS 100 as described above. The particular PBS 100 construction for use in the tab member 42 and the slot member 44 may be the same or different.

A benefit of using the PBS 100 in the construction of the tab member 42 and/or slot member 44 can be appreciated during fastening of the tab member 42 and the slot member 44. The tab member 42 comprising the PBS 100 can exhibit preferential bend. Qualitatively, the PBS 100 allows the tab member 42 to be more pliant (i.e., greater deflection) in one direction but less pliant in the opposing direction (i.e., less deflection). As discussed above, directional pliancy of the tab member 42 (or slot member 44) may be advantageous since it improves the comfort of the article being fastened (e.g., the tab member bends with the wearer). However, if the tab member 42 did not have the preferential bend capability of the PBS 100, the tab member 42 could bend indiscriminately (i.e., the tab member would bend out of the x-y plane upon application of a $+F_z$ or a $-F_z$). Such indiscriminate bending by the tab member 42 is undesirable in a tab and slot type fastener. With a product like a diaper or a training pant, an infant may be unable to fasten the tab member 42 if it does not have some rigidity in one direction. Using the PBS 100 to construct the tab member 42 and/or the slot member 44 imparts a degree of rigidity in one direction to the member without sacrificing the ability of the member to bend in the other direction.

A fastening system 40 having an engaging member 41 and/or a receiving member 43 comprising the PBS 100 is particularly beneficial when the fastening system 40 is placed in a compressive region or expansive region. A compressive region of the wearer is a region in which the natural bodily movement of the wearer will move towards the region. An expansive region of a wearer is a region in which the natural body movement of the wearer will move away from the region. There are several compressive and expanding regions on the body of a wearer, especially where there are joints that bend such as knees, elbows, shoulders, hips, ankles, wrists, etc. In order to determine whether a particular region of the body is a compressive or expanding zone within the scope of the present invention, the change in the surrounding anatomical structure of the region is examined as a joint is moved from a "neutral" position to a bent position. A neutral position is defined as the position when the joint is not bent (i.e., the position with the muscles generally relaxed and not attempting to flex the joint). If the surrounding anatomical structure, e.g., tissues, bones, etc., would tend to compress or bend an object on the body's surface as the joint is moved from a neutral to a flexed position, the region is defined as a compressive region. If the surrounding anatomical structure would tend to expand or stretch an object on the body's surface, the region is defined as an expanding region.

FIG. 8A shows a top down view (i.e., a head-to-toe view) of a wearer 90 bisected at the waist. In this example, several regions are shown which are of interest for the application of a diaper and fastening system 40 placement. A back region, B, denotes a region across the back of the wearer 90, which may include a portion of the tissues and muscle associated with the buttocks; A first side region and second side region, S1 and S2, denote side regions of the wearer 90; and a front region, F, denotes the front or pubic region of the wearer. FIG. 8B shows a side view of a wearer 90 in the "neutral" position for the hip joint in which the wearer's back and legs are generally in a vertical orientation. FIG. 8C shows a side view of the wearer in a bent position in which the wearer's legs have been raised to a generally horizontal orientation. The front region and/or the side regions S1 and S2, for example, are compressive because the distance between two points (S, S) on the skin surface in the region becomes smaller as the wearer's leg lifts or the wearer bends at the waist. In the back region B, behind the legs of the wearer, however, the distance between two points (B, B) on the skin of the wearer tends to increase in all but extreme rearward leg motions. With respect to a diaper for application on babies, motions such as sitting and leaning forward are more prevalent, and, thus, the back region B is typically considered an expanding region because these motions result in the distance between two points on the skin of the wearer increasing. In extreme rearward leg motions such as when the leg moves substantially backward and the back is held vertical, the distance between two points on the skin of the wearer may decrease. However, such extreme rearward leg movement is much less likely to occur than the legs being brought forward or the wearer leaning forward, particularly when the wearer is a baby or infant. Knowledge of the compressive and expansive regions may be applied to the placement of the tab members and slot members for articles other than diapers such as, but not limited to, sanitary napkins, bibs and wraps placed on other parts of the wearer.

Figure 9A:
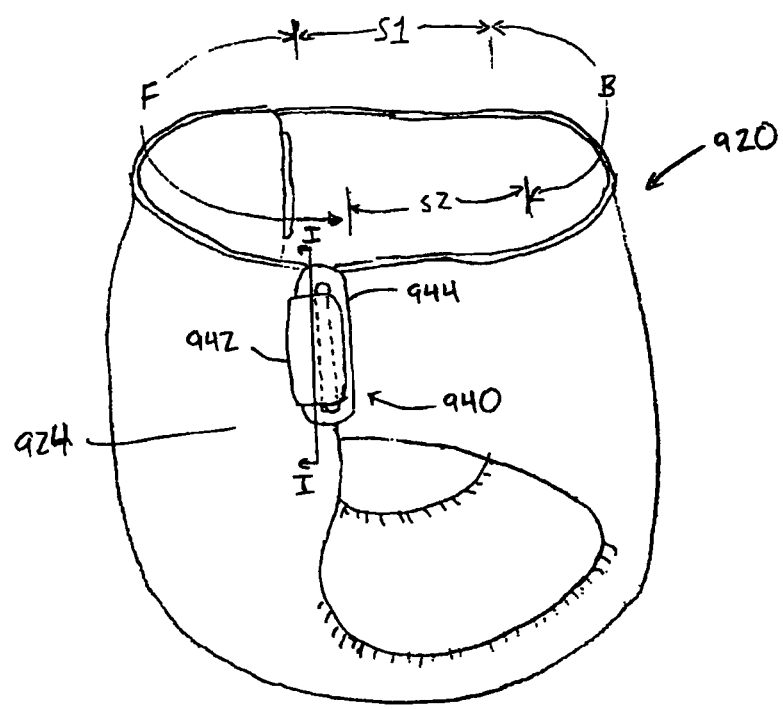
FIG. 9A is a perspective view of a diaper with a fastening system disposed in the front region of a wearer.

In certain embodiments, a diaper may have a fastening system that is within the compressive region of the wearer during normal wear. FIG. 9A depicts a diaper 920 with a fastening system 940 disposed in the front region F of the wearer. The fastening system 940 is shown having a tab member 942 and a slot member 944. The tab member 942 and/or the slot member 944 may comprise a PBS. The front region F, back region B, and side regions S1 and S2, from FIG. 8A are superimposed on the diaper 920 of FIG. 9a. In constructing the tab member 942 and slot member 944, the PBS may be disposed such that the preferential direction of bend exhibited by the PBS coincides with the bend of the wearer in the front region F. For example, with a PBS exhibiting preferential bend toward the auxiliary layer, the auxiliary layer would be disposed as the garment-facing surface of the tab member 942 and/or slot member 944. FIG. 9B is a cross-sectional view of the fastening system 940, which is taken along sectional line I-I of FIG. 9A, showing the system 940 subjected to a compressive force such as can occur when the wearer of the diaper 920 sits down. The PBS imparts to the tab member 942 and slot member 944 the ability to bend with the wearer. While not shown, it should be apparent that the fastening system 940 may be located in an expansive region of the wearer, such as the rear region R. In the expansive region, the tab member 942 and a slot member 944 comprising a PBS may be oriented to bend with the wearer.

FIG. 10A depicts another suitable embodiment incorporating a fastening system using the PBS. FIG. 10A illustrates a wrap 1020 that may be placed around a portion of a wearer. The wrap 1020 is shown as being disposed around an arm 1012 of the wearer and covering the elbow joint 1014. Clearly, the size and shape of the wrap 1020 could be modified so that it could encircle other portions of the wearer's body such as the wrist, shoulder, knee, ankle, waist, neck, chest, midriff, and other like areas such areas having compressive and/or expansive regions. The wrap 1020 may be of any size and/or shape and may be made from any suitable material known including, but not limited to, neoprene, elastomeric scrims, woven and nonwoven webs, and the like. The wrap 1020 may comprise a fastening system 1040. The fastening system 1040 is shown as having a tab member 1042 and a slot member 1044 having a slot 1046 there through. In a simple form, the fastening system 1040 is fastened by passing the tab member 1042 completely through the slot 1046 of the slot member 1044. The tab member 1042 and/or the slot member 1044 may comprise the PBS as described above. As shown in FIG. 10A, if the tab member 1042 and slot member 1044 are disposed in a compressive region 1016 of the elbow 1014 (i.e., inner surface of the elbow 1014), the PBS should be oriented to mirror the bend of the elbow 1014. Likewise, as shown in FIG. 10B, if the tab member 1042 and slot member 1044 are disposed in an expansive region 1018 of the elbow 1014 (i.e., outer surface of the elbow), the PBS 100 should be oriented to mirror the bend of the elbow 1014. For example, with a PBS exhibiting preferential bend toward the auxiliary layer, the auxiliary layer would be disposed as the garment-facing surface of the tab member 1042 and/or slot member 1044 in FIG. 10A and disposed as the body-facing surface of the tab member 1042 and/or slot member 1044 in FIG. 10B.

In another suitable embodiment, a medical product may include a fastening system 1140 having a tab member 1142 and a slot member 1144 wherein the tab member 1142 and/or slot member 1144 include a PBS. Medical products include a wide variety of items such as surgical gowns and drapes, face masks, head coverings, shoe coverings, wound dressings, bandages and sterilization wraps which as disclosed in further detail in U.S. Pat. No. 5,540,976. FIG. 11 shows a front view of a surgical gown 1120 with a fastening system 1140 including a tab member 1142 and slot member 1144 that may comprise the PBS. The fastening system 1140 is shown in the front waist region of the surgical gown which may be a compressive region. One skilled in the art will readily appreciate that the fastening system 1140 may be located in other areas of the surgical gown 1120 including other compressive regions and/or expansive regions. Furthermore, its should be readily appreciated that the fastening system 1140 may be use on other types of garments and, particularly, tight-fitting garments.

Figure 12A:
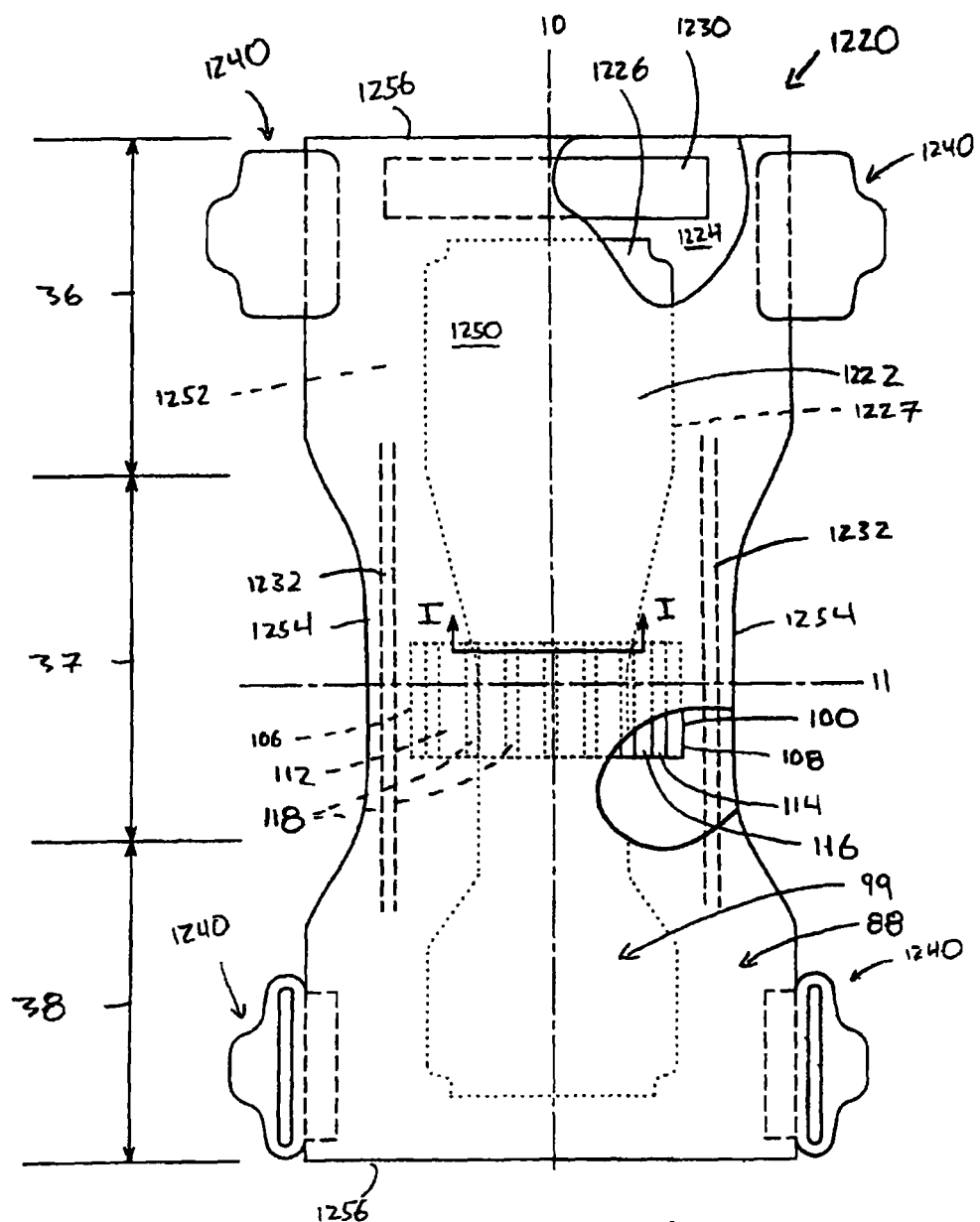
FIG. 12A is a plan view of a suitable absorbent article in a flat, unfastened configuration shown partly in section, and having a portion of the structure being cut-away to show underlying detail.

While the embodiments presented above describe the PBS as a component of a fastening system, the PBS may provide other unique benefits outside of the realm of fasteners. The PBS may be used within any commercial good (e.g., an absorbent article, medical product, wrap, etc.) where it is desirable for a substrate, material, or laminate to deform more in one direction versus an opposing direction. For example, FIG. 12A depicts plan view of a diaper 1220 with cut-aways to show underlying detail. The diaper 1220 may comprise a liquid pervious topsheet 1222; a backsheet 1224 joined with the topsheet 1222; an absorbent core 1226 (having a core perimeter 1227) positioned between the topsheet 1222 and the backsheet 1224. The diaper 1220 may also have leg cuffs 1232, a waist feature, 1230 and a fastening system 1240. The diaper 1220 also has longitudinal edges 1254 and lateral edges 1256. The diaper 1220 is shown to have an garment-facing surface 1252, an body-facing surface 1250 opposed to the garment-facing surface 1252, first waist region 36, a second waist region 38 opposed to the first waist region 36, and a crotch region 37 positioned between the first waist region 36 and the second waist region 38. The diaper 1220 also comprises a perimeter region 88 and a central region 99. The perimeter region 88 is a portion of the diaper 1220 outboard of the core perimeter 1227. The central region 99 is a portion of the diaper 1220 inboard of the core perimeter 1227. The diaper 1220 is shown having a longitudinal centerline 10 and a lateral centerline 11.

Figure 12B:
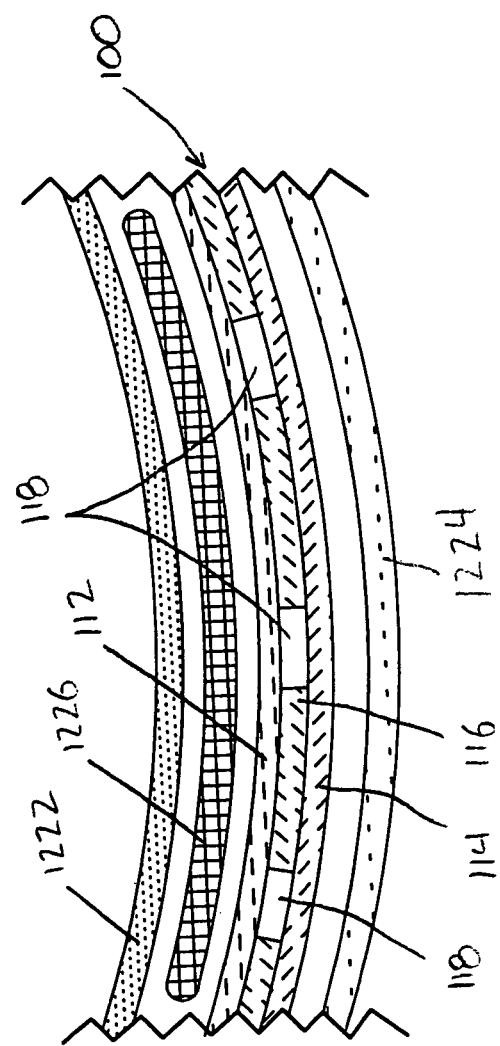
FIG. 12B is a cross-sectional view of the absorbent article of FIG. 12B taken along sectional line I-I.

A PBS 100 may be disposed in any suitable location in the diaper 1220 (e.g., on the topsheet 1222, between the topsheet 1222 and the core 1226, in the core 1226, between the core 1226 and the backsheet 1224, on the backsheet 1224, etc.). Alternatively, the PBS 100 may be part may be constructed to be any diaper component or to be a portion of any diaper component (e.g., the topsheet 1222, the core 1226, the backsheet 1224, etc.). The PBS 100 may be disposed in any suitable region (e.g., first waist region 36, and a crotch region 37, second waist region 38, perimeter region 88, and/or central region 99) of the diaper 1220 or the PBS 100 may be disposed in one or more regions of the diaper 1220. The PBS 100 may be positioned such that the diaper 1220 will maintain an ideal shape during wear. As shown in the embodiment depicted in FIG. 12A, the PBS 100 may be positioned within the crotch region 37 of the diaper 1220. The PBS 100 may have a first edge 106 and a second edge 108. The PBS 100 may be positioned such that the first edge 106 and the second edge 108 of the PBS 100 are proximate and approximately parallel to the longitudinal edges 1254 of the diaper 1220. The PBS 100 is shown with a base layer 112, an auxiliary layer 114, and an intermediate layer 116 there between. In this embodiment, void regions 118 are shown and the PBS 100 exhibits preferential bend toward the base layer 112. However, any PBS 100 within the scope of this invention may be used. FIG. 12B is a cross-sectional view of the diaper 1220 taken along sectional line I-I of FIG. 12A; FIG. 12B shows the diaper during wear. The PBS 100 is oriented such that it may deform out of the x-y plane to form a "U" shape upon application of a deforming force. The deforming force may be exerted by the leg cuffs 1232, which may be elasticized, or by the legs of the wearer. It is desirable for the crotch region 37 of the diaper to maintain a "U" shape during wear to provide improved absorbency and leakage prevention. By maintaining the "U" shape, any body exudates will collect down in the crotch region 37 where the core is present. If the crotch region 37 were inverted in shape (e.g., an upside-down "U" shape), body exudates may gather at the edges of the diaper such as in proximity to the leg cuffs 1232. Such a design may exacerbate leakage through or around the cuff 1232. However, in certain other absorbent article embodiments, it may be desirable for the crotch region 37 to be inverted relative to the orientation shown in FIG. 12B (i.e., crotch region 37 exhibits an upside-down "U" shape). The PBS 100 may be utilized to maintain such a shape.

Figure 13:
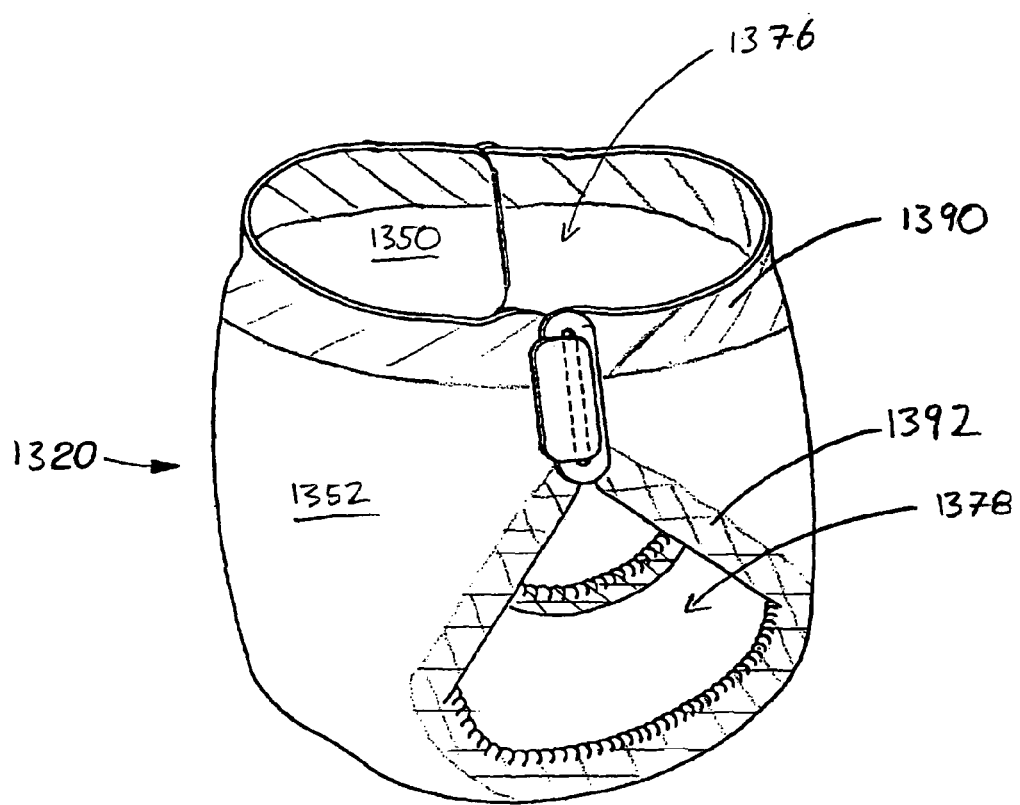
FIG. 13 is a perspective view of an absorbent article having a waist gasketing region and a pair of leg gasketing regions.

In yet another embodiment, the PBS 100 may be used along, adjacent to, or proximate to a gasketing region of a diaper 1320. Gasketing regions are those portions of the diaper 1320 that are adjacent to an opening in the diaper 1320 such as the waist opening 1376 or a leg opening 1378. FIG. 13 depicts a waist gasketing region 1390 adjacent the waist opening 1376 and a pair of leg gasketing regions 1392 adjacent the leg openings 1378. A PBS 100 may be located partially or fully within the waist gasketing region 1390 and/or the leg gasketing regions 1392. The PBS 100 may be oriented such that the relative preferential bend goes inward toward the body of a wearer or outward away from the body of the wearer. In a suitable embodiment, the PBS 100 may be disposed at least partially within the waist gasketing region 1390 and/or the leg gasketing regions 1392 such that the PBS 100 preferentially bends away from the wearer's body to avoid rolling inward. Alternatively, the PBS 100 may preferentially bend away toward the wearer's body to avoid rolling outward. The PBS 100 may be located on a body-facing surface 1350 or a garment-facing surface 1352 of the diaper 1320. Alternatively, the PBS 100 may be disposed within the layers of the diaper 1320 (e.g., between the topsheet and backsheet).

Figure 14A:
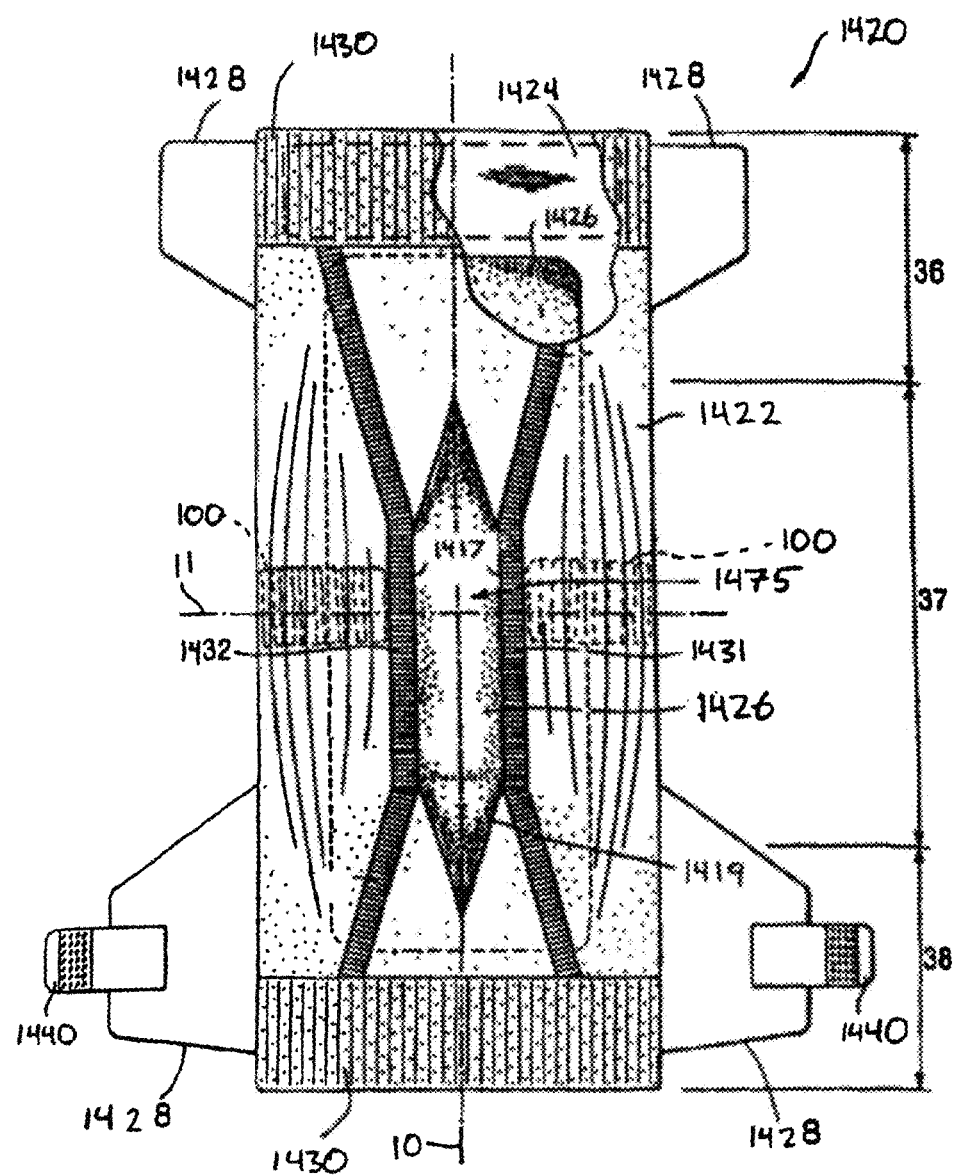
FIG. 14A is a plan view of a suitable absorbent article in a flat, unfastened configuration shown partly in section, and having a portion of the structure being cut-away to show underlying detail.

In another suitable embodiment, the PBS 100 may be used as or combined with an elasticized topsheet. FIG. 14A is a plan view of a suitable diaper 1420 having an elasticized topsheet 1422 with a slit opening 1419 there through. The diaper 1420 is shown having a longitudinal centerline 10 and a lateral centerline 11. The diaper 1420 is shown to have a first waist region 36, a second waist region 38, and a crotch region 37 disposed between the first waist region and the second waist region. The diaper 1420 may have a backsheet 1424, side panels 1428, a fastening system 1440, and a waist feature 1430. The slit opening 1419 may have longitudinal edges 1417. The slit opening 1419 may be located so that fecal exudates pass through the slit opening 1419 and into a void space 1475 formed between the elasticized topsheet 1422 and an absorbent core 1426 below. Other substrates may be disposed between the elasticized topsheet 1422 and the absorbent core 1426 if it is undesirable for certain bodily exudates to directly contact the core 1426. The elasticized topsheet 1422 may comprise elastic members 1431, 1432. The elastic members 1431, 1432 may be located along at least a portion of the longitudinal edges 1417 of the slit opening 1419. The elastic members 1431, 1432 may allow the longitudinal edges 1417 of the slit opening 1419 may be held against the wearer's skin allowing the feces to penetrate the slit opening 1419 without deflection. The elastic member 1431, 1432 may assist in maintaining the elasticized topsheet 1422 in close contact to the wearer's skin. The elastic member 1431, 1432 also may assist in maintaining the position of the slit opening 1419 along a gluteal groove and perianal region. In certain embodiments, a PBS 100 may be positioned on the elasticized topsheet 1422 such that the PBS 100 will maintain an appropriate curvature around a wearer's buttocks.

Figure 14B:
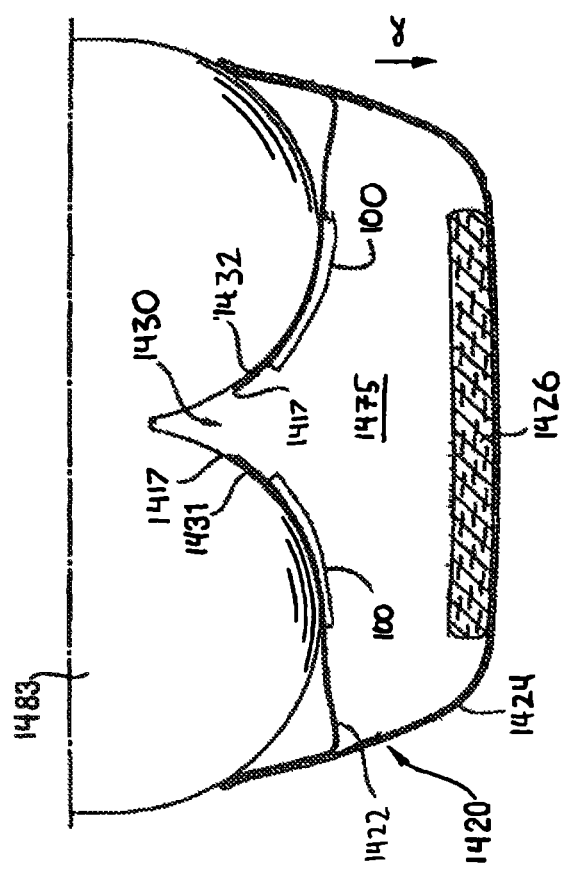
FIG. 14B is a cross-sectional view of the absorbent article of FIG. 14A taken along the lateral centerline while the article is in wear.

FIG. 14B is a cross-section of the diaper 1420 taken along the lateral center line 11 of FIG. 14A while the diaper 1420 is in wear on a wearer 1483. The elasticized topsheet 1422 is held in position, in part, by the elastic members 1431, 1432. The PBS 100 is positioned such that the PBS will bend about the wearer's buttocks. The PBS 100 ideally resists deflection out of the plane in response to a force in the α-direction shown in FIG. 14B. The PBS 100 imparts a degree of rigidity to the elasticized topsheet 1422. This prevents the elasticized topsheet 1422 from deflecting downward which may result in inadvertent deposit of bodily exudates onto the elasticized topsheet 1422 rather than through the elasticized topsheet 1422. One or more PBSs 100 may be used in the diaper 1420. Furthermore, the PBS 100 may be joined to the body-facing surface or the garment-facing surface of the elasticized topsheet 1422 or the PBS 100 may be disposed between two or more substrates that form the topsheet 1422.

Figure 15A:
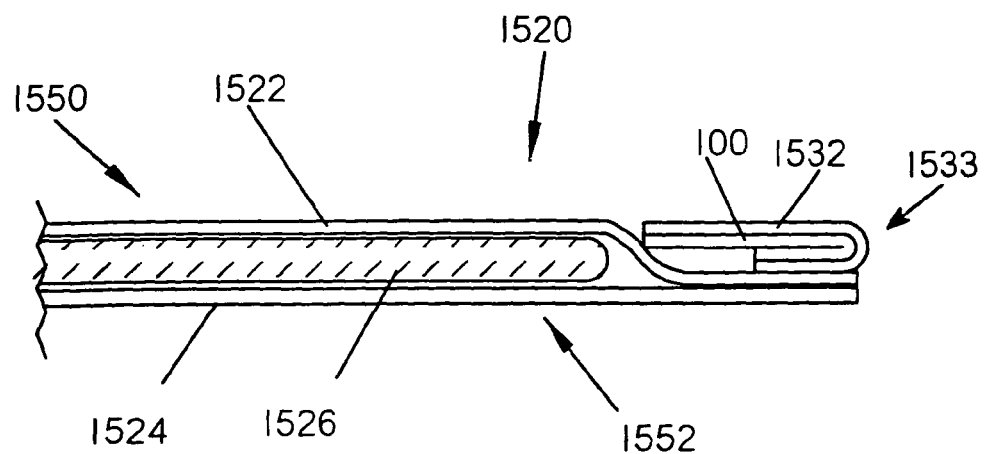
FIG. 15A is a partial cross-sectional view of an absorbent article with a barrier leg cuff in a compressed state.
Figure 15B:
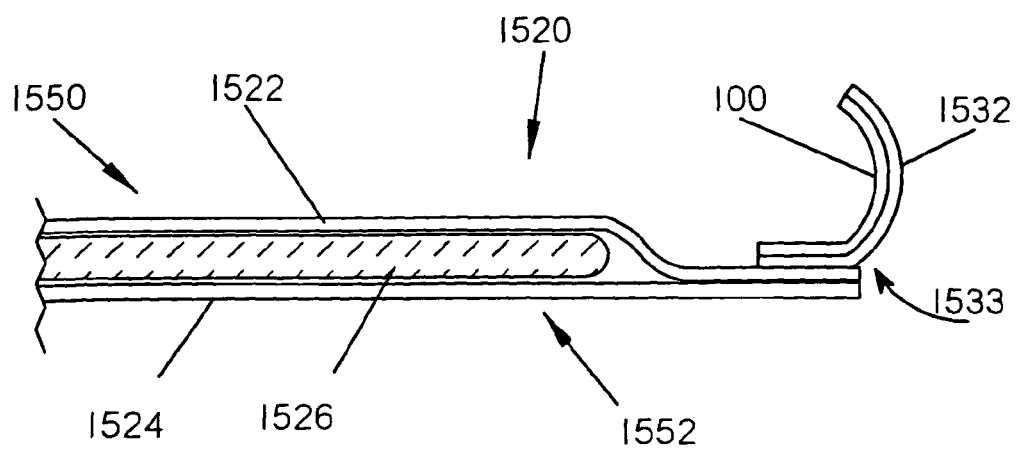
FIG. 15B is a partial cross-sectional view of an absorbent article with a barrier leg cuff in an extended state.

In another suitable embodiment, a PBS 100 may be used as or combined within a barrier leg cuff. FIGS. 15A-B are cross-sectional views of a diaper 1520 taken approximately along the lateral centerline. The diaper 1520 has garment-facing surface 1552 and a body-facing surface 1550. The diaper 1520 is shown to have a topsheet 1522, a backsheet 1524, and an absorbent core 1526 disposed there between. A barrier cuff 1532 is shown and may be joined to the body-facing surface 1552 of the diaper 1520 or to other suitable locations of the diaper 1520. Barrier cuff 1532 construction has been detailed above as well as in the previously mentioned U.S. Pat. Nos. 4,909,803 and 4,695,278. The PBS 100 may be a discrete structure disposed on the barrier leg cuff 1532, as shown in FIGS. 15A-B. Alternatively, the barrier cuff 1532 may be formed from the PBS 100 (i.e., the PBS 100 is integral to the barrier cuff 1532). The PBS 100 of FIGS. 15A-B is shown having a preferred bend inboard toward the core 1526. However, it should be readily appreciated that the PBS may be oriented such that the preferred bend is inverted (i.e., away from the core 1526).

FIG. 15A shows the diaper 1520 in a compressed state such as when the diaper 1520 is contained within a package. In the compressed state, the barrier cuff 1532 and PBS 100 are folded toward the core. The folded barrier cuff 1532 and the PBS 100 may yield one or more fold regions 1533. The fold region 1533 enables the barrier cuff 1532 and the PBS 100 to fold over. This allows the diaper 1520 to assume a relatively planar state which reduces diaper 1520 volume thereby improving shipping and packaging efficiency. Once the diaper 1520 is removed from the compressed state, portions of the barrier cuff 1532 and PBS 100 can extend upwardly away from the body-facing surface 1550 of the diaper 1520. In the extended configuration of FIG. 15B, the barrier cuff 1532 is in an ideal position to serve as a barrier to bodily exudates that may move outwardly from the body-facing surface 1550 of the diaper 1520. The PBS 100 enables the barrier cuff 1532 to transition from the compressed state of FIG. 15A to the extended state of FIG. 15B. The PBS 100 may be constructed to allow sufficient bend or flexibility so that the PBS 100 can folded onto itself in the preferential bend direction. However, the PBS 100 of this embodiment resists outboard bending (e.g., curvature away from the core). The resistance to outboard bending by the PBS 100 may allow the barrier cuff 1532 to maintain containment. It should be recognized that a PBS 100 exhibiting the ability to fold upon itself is not limited to this barrier cuff embodiment; such a PBS 100 may be used in as the PBS in other embodiments of the present invention.

Figure 16B:
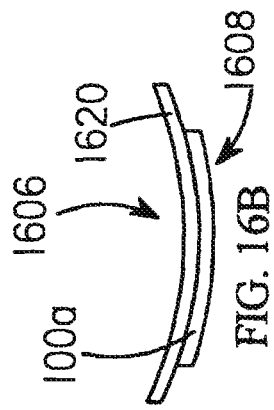
FIGS. 16B-D are cross-sectional views of the absorbent pad of FIG. 16A taken through sectional lines I-I, II-II, and III-III, respectively.
Figure 16C:
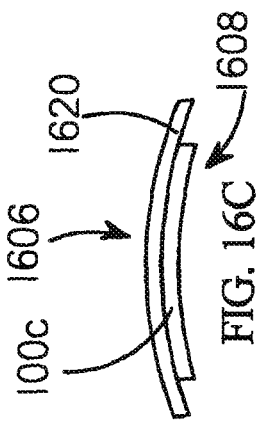
Figure 16D:
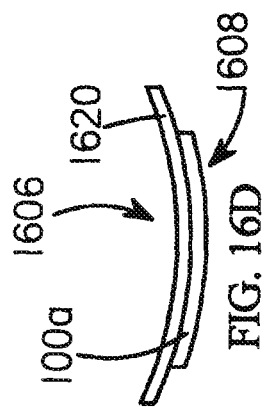
Figure 16A:
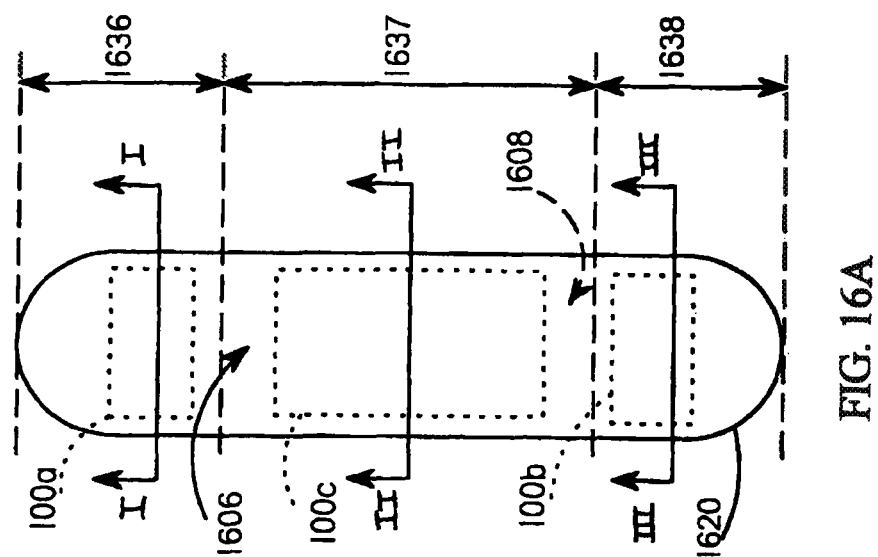
FIG. 16A is a plan view of an absorbent pad comprising multiple preferential bend structures.

In another suitable embodiment, multiple PBS 100 may be incorporated into a consumer and commercial good so as to provide the good with multiple preferential directions of bend. FIG. 16A illustrates an absorbent pad 1620 such as may be used as a sanitary napkin or with a diaper. The absorbent pad may have a body-facing surface 1606 and an opposing garment-facing surface 1608. The absorbent pad 1620 may comprise at least two PBSs 100. The absorbent pad 1620 may comprise two or more regions. The absorbent pad 1620 of FIG. 16A is depicted as having three regions: a first end region 1636, a second end region 1638, and an intermediate region 1637 between the first end region 1636 and the second end region 1638. Typically, the first end region 1636 is intended to be oriented to the front of a wearer and the second end region 1638 is intended to be oriented to the back of the wearer. Each region may comprise a PBS 100; however, certain regions may lack a PBS 100. In FIG. 16A, the absorbent pad 1620 comprises three PBSs: a first PBS 100*a* in the first end region 1636, a second PBS 100*b* in the second end region 1638, and a third PBS 100*c* is the intermediate region 1637. While each PBS 100*a*, 100*b*, and 100*c* are shown contained within the respective region, it should be recognized that the PBS may span one or more regions.

One or more of the PBSs 100*a*, 100*b*, and 100*c* may be constructed in a similar manner or each PBS may be structurally and compositionally distinct. Furthermore, one or more of the PBSs 100*a*, 100*b*, and 100*c* may share the same direction of preferential bend. In one suitable embodiment, the direction of preferential bend may differ in the intermediate region 1637 compared to the first end region 1636 and the second end region 1638. FIG. 16B-D are cross-sectional views taken through the first end, intermediate, and second end regions 1636, 1637, 1638, respectively. FIG. 16B is a cross-section taken along sectional line I-I in FIG. 16A. FIG. 16B shows the first end region 1636 with the first PBS 100a having a preferential bend toward the body-facing surface 1606. FIG. 16C is a cross-section taken along sectional line II-II in FIG. 16A. FIG. 16C shows the intermediate region 1637 with the third PBS 100c having a preferential bend toward the garment-facing surface 1608. FIG. 16D is a cross-section taken along sectional line III-III in FIG. 16A. FIG. 16D shows the second end region 1638 with the second PBS 100b having a preferential bend toward the body-facing surface 1606. The absorbent pad 1620 with the zoned preferential bend as illustrated in FIGS. 16B-D is particularly desirable in sanitary napkins. A common problem with sanitary napkins is maintaining the napkin in close contact to the body of the wearer. Having an intermediate region 1637 that preferentially bends toward the garment-facing surface 1608 can aid in improving the functionality of the napkin. However, it should be recognized that may other embodiments of an absorbent pad 1620 having multiple regions, multiple PBSs, and/or multiple directions of preferential bend may be constructed and are within the scope of the present invention.

In some embodiments, the curvature desired in the consumer or commercial good may be highly complex. For example, to follow and make intimate contact with the complex anatomy of the female pudendal region, multiple directions of preferential bend may be required from one region to the other and within a given region. FIG. 16E illustrates an absorbent pad 1620 such as may be used as a sanitary napkin or with a diaper. The absorbent pad may have a body-facing surface 1606 and an opposing garment-facing surface 1608. The absorbent pad 1620 may comprise at least two PBSs 100. The absorbent pad 1620 may comprise two or more regions. The absorbent pad 1620 of FIG. 16E is shown having a first end region 1636, a second end region 1638, a central intermediate region 1637a, and opposing lateral intermediate regions 1637b. Typically, the first end region 1636 is intended to be oriented to the front of a wearer and the second end region 1638 is intended to be oriented to the back of the wearer. The absorbent pad 1620 may comprise one or more PBSs wherein each PBS has the same or different direction of preferential bend. In the embodiment shown in FIGS. 16E-H, the absorbent pad is shown having a PBS in each region. The first end region 1636 comprises a PBS 100d which may exhibit a preferential bend toward the body-facing surface 1606 as shown in the cross-sectional view of FIG. 16F (taken along sectional line IV-IV in FIG. 16E). The second end region comprises a PBS 100e which may exhibit preferential bend toward the garment-facing surface 1608 as shown in the cross-sectional view of FIG. 16G (taken along sectional line V-V in FIG. 16E). The central intermediate region 1637a may comprise a PBS 100f that exhibits a preferential bend toward the garment-facing surface 1608. The lateral intermediate regions 1637b each may comprise a PBS 100g that exhibits a preferential bend toward the body-facing surface 1606. The central intermediate region 1637a with the PBS 100f and the lateral intermediate regions 1637b with the PBSs 100g are shown in the cross-section view of FIG. 16H (taken along sectional line VI-VI in FIG. 16E). Regions with differing directions of bend may be achieved by having multiple PBSs throughout the structure as shown in FIG. 16E or by having one or more PBSs capable of preferential bending in more than one direction, such as shown in the embodiments of FIGS. 3A-D.

Test Methods

Preferential Bend Test Method—The preferential bend test method measures the load required to deflect a sample through a range of bending about the X-axis of a sample. It should be recognized that a sample may bend about more than one axial line; this test measures preferential bend about one axial line. However, the test may be repeated to measure preferential bend about other axial lines. This test can be used to compare samples deflected in the positive Z direction and in the negative Z direction by comparing the resultant loads at a given extension, and then determining the percent difference between the values. For FIGS. 17A-C, the axial designations provided in the figures are to be taken as affixed to the sample such that rotation of the sample implies rotation of the axial designations.

Figures 17A, 17B:
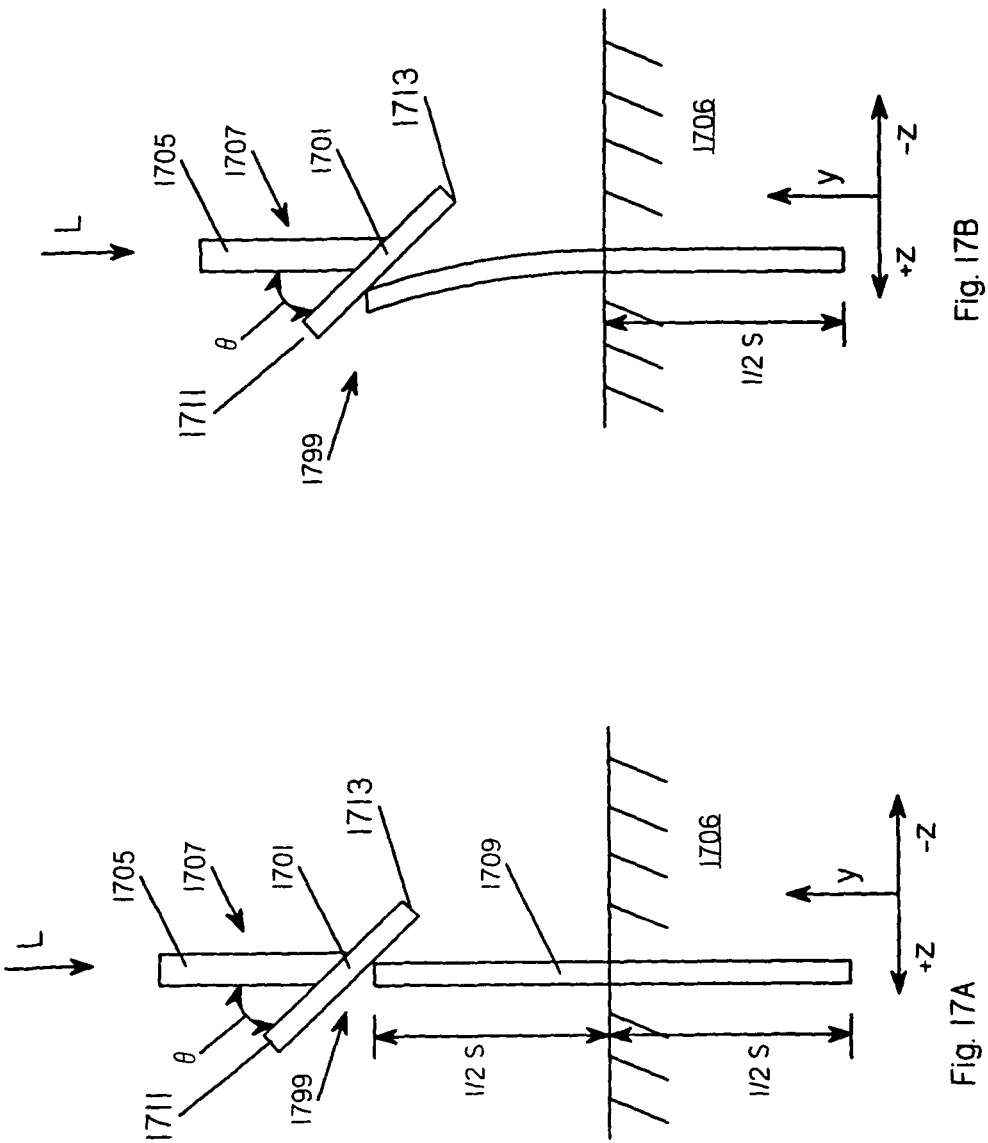
FIGS. 17A-C depict a suitable sample and instrument configuration for the Preferential Bend Test Procedure.

A test fixture 1799 for measuring preferential bend is shown in FIG. 17A and FIG. 17B. The test fixture includes a foot 1701, a measuring device 1707, and a test sample holder 1706. The preferential bend test method measures the load required to deflect a fastening device sample 1700 through a range of bending deflection using the foot 1701 that deflects the sample 1700 with foot 1701 at an angle θ of 45 degrees.

The preferential bend test method may be used to measure the bending capabilities of samples in the positive Z and negative Z directions. One way to do this is to have the foot 1701 deflect the sample by contacting the sample and traveling a given distance in the Y direction toward the sample. The range of deflective loads applied to the sample 1700 by the foot 1701 may be between about 0 grams and about 1.5 kilograms (kgf). The method measures the force to deflect the sample 1700 as a function of the deflection of the sample in grams-force applied. The test continues until the sample 1700 reaches a maximum load of 1500 grams-force or the foot 1701 travels a distance equal to 25% of the sample length as measured from the point of contact with the sample 1700, whichever comes first.

Figure 17C:
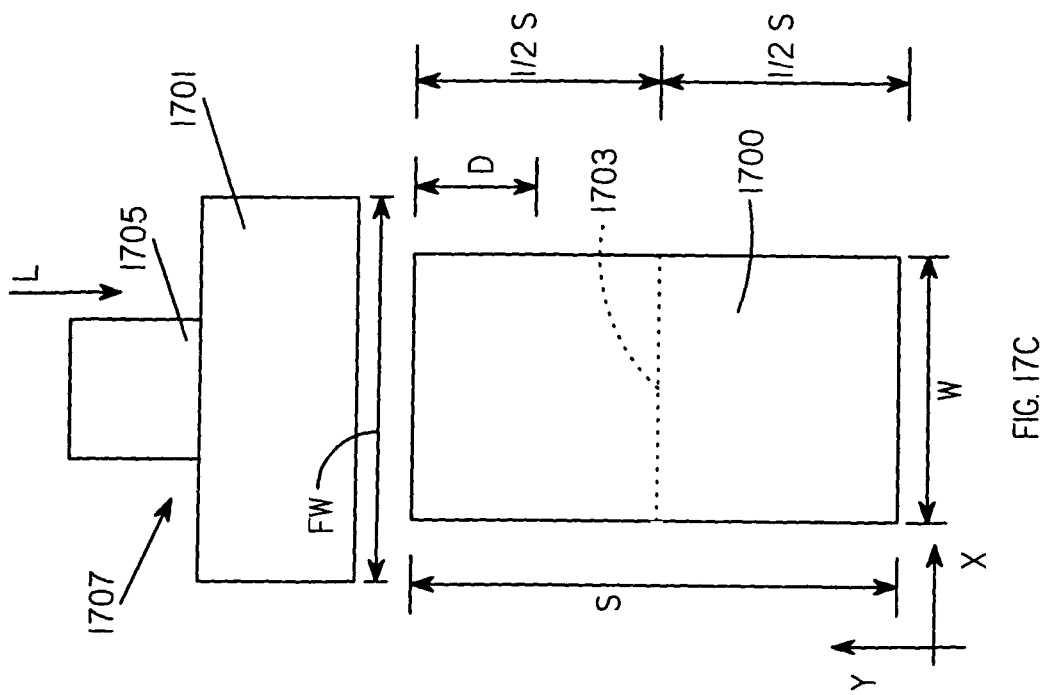

FIG. 17C shows a plan view of the sample 1700, the foot 1701, and the measuring device 1707. If the sample 1700 is a component of a product, the sample 1700 must be removed from the product. The sample 1700 may be cut from of the product along with any portions of the product that are related to the performance of the laminate 1700. Some amount of material comprising the product and surrounding the sample 1700 may be retained on the sample 1700 so the integrity of the sample 1700 is maintained, yet the material retained does not significantly affect performance of the sample 1700. Otherwise, the sample 1700 should be carefully removed from the product minimizing the retention of excess material to within 1 mm of the edges of the sample. If extra material is present, the extra material should be of equal length opposing ends and/or sides of the sample 1700. The extra material should not be included in the measurement of the sample length.

The sample length S shown in FIG. 17C is defined as the measurement of the sample 1700 that is parallel to a primary direction of the displacement of the foot (as shown along the Y-axis of the sample 1701) and does not include any excess material from the product not removed from sample 1701. This provides consistency over the broad range of laminates applicable to this method. Length S is measured to the nearest 1 millimeter. Twenty-five percent of measured length S is defined as the range of deflection, D. D is the distance at which the foot would cease deflecting the sample 1701 if the load of 1500 grams-force had not been exceeded. The sample width W is defined as the measurement of the sample 1700 parallel to the x-axis.

The centerline 1703 of the laminate is identified and marked within 1 millimeter. Centerline 1703 is defined as the line that crosses the Y-axis of the laminate 109 coinciding with 50 percent of sample length S and parallel to the X-axis.

The testing apparatus can be any suitable tensile and compressive testing system capable of holding a sample, setting the appropriate gage length, moving the foot 1701 at a controlled rate and direction, and measuring the resulting load of the part onto the foot 1701 while allowing the sample to bend freely without touching any portion of the apparatus other than foot 1701 or sample holder 1706. An example of a suitable test apparatus is an MTS Synergie 200 Tensile Tester model number SYN200 equipped with a computer interface having TestWorks™ for Windows™ by MTS™ version 3.10 or later, outfitted with suitable load cell and flat grip faces capable of holding the sample without slippage during the test. A suitable load cell is sized to measure loads between 10% and 90% of load cell capacity, for example use of a 100 Newton Load Cell for a peak load of 1500 grams-force. The test apparatus must be located in a temperature and humidity controlled environment, or must be capable of holding the samples in a controlled environment. Controlled conditions are to be 22° C.+/−2° C. and 50%+/−10% relative humidity.

The foot 1701 is a bar that measures about 25 millimeters (mm) wide (designated FW in FIG. 17C) by about 70 mm long and is about 12 mm thick. If the sample width W is greater than 20 mm, the foot width FW is increased to be the sample width plus 5 mm. The foot is made of steel with the surface which contacts the sample 1700 polished to a mirror finish of (approximately 2-4 microns surface finish). The foot 1701 must be protected from any scrapes, nicks, or gouges so that the mirror finish is maintained and the sample 1700 may slide readily on foot 1701 during the testing. The foot 1701 has a front edge 1711 and a rear edge 1713. If, during the test, any portion of the sample 1700 extends beyond the front edge 1711 of foot 1701 as the sample bends, a longer foot must be used, and the data obtained with the original foot must be discarded. The foot 1701 is connected to a rod 1705 that is attached about 15 mm from the back edge 1713 of the foot and at a 45°±2° angle to the contacting surface of the foot. The rod 1705 is about 45 mm long at the longest point from the locking collar to the attached foot 1701. The rod 1705 is designed to fit the tensile tester's top fixture with a locking collar and a cotter pin to minimize any wobble. Test sample holder 1706 is designed to fit in the tensile tester's bottom fixture with a locking collar to minimize any wobble. When foot 1701 and test sample holder 1706 are placed properly in the tensile tester, the center of the rod 1705 will be aligned approximately evenly with the center of sample 1700 at point of contact when viewed from the side as shown in FIG. 17A. The test is designed to begin with the foot 1701 just in contact with sample 1700 at a distance equal to one half of S from the sample centerline 1703 and to terminate either at the load L test limit of 1500 grams force or when of the foot 1701 has traveled a distance of 25% of the sample length S, whichever comes first.

Testing begins by zeroing the load on the measuring device 1707 with the fixtures and foot 1701 in place, but prior to placing the sample 1700 in the test fixture 1799.

As shown in FIG. 17A, the sample 1700 should be placed in the test sample holder 1706 such that half of sample 1700 is above the test sample holder 1706 when viewed from the side as in FIG. 17A (the centerline 103 may assist in determining when half of the sample 1700 is loaded in the cell). The foot 1701 is centered on the sample width when viewed from the surface of the xy-plane as in FIG. 17C so that width of the foot 1701 extends beyond each of the opposing longitudinal sides 1702 of the sample. The orientation of the sample should be such that the foot 1701, upon contacting and deflecting the sample will deflect the sample 1700 in the positive Z direction. The gripping location of the test sample holder 1706 should be precise within about 1 mm of true centerline 103 of the sample 1700. The sample 1700 should also be centered under the foot 1701 and in the test fixture 1799. The starting position of the foot 1701 should be about 15 mm away from the sample, then the polished face of the foot 1701 should be brought into contact so that it is just visually touching the fastening device sample 1700 and is producing only a very small load of less than 0.9 grams as shown in FIG. 17A. The crosshead position of the tensile tester is then zeroed and the test is run by moving foot 1701 down at a constant rate of 100 millimeters/minute. The test continues as fastening device sample 1700 deflects under load until the test terminates either at the load L test limit of 1500 grams force or when the traveled distance of the foot 1701 from point of contact of the sample 1700 exceeds 25% of the sample length S, whichever comes first. Upon termination of the test, the foot 1701 is immediately retracted to its original position prior to contacting the sample 1700.

The output data is load versus foot travel distance for the first direction of bending and is recorded as load $L_1$ vs. travel of foot 1701 $D_1$ from point of contact to test termination. Load $L_1$ and distance $D_1$ are recorded for at least about every 0.5 millimeters of foot 1701 travel $D_1$, and preferably at least every 0.1 millimeters of travel to create a smooth curve or line.

At this point the test must be repeated to attain the output data with the sample 1700 tested in the negative Z direction. As damage to the sample 1700 may have occurred during the first portion of the test, it is required that a substantially identical second sample which has been prepared in a substantially identical fashion is used for this portion. The second sample is randomly selected from a group of samples created in the course of normal production in which each sample is believed to be produced identically (or within normal manufacturing tolerances) such that the first and second samples are substantially identical. The second sample 1700 should be placed in the test sample holder 1706 and the orientation reversed with respect to the first sample such that, upon contact and deflection of the second sample 1700 by the foot 1701, the second sample is deflected in the negative Z direction. The reversal of the orientation should consist of a 180° rotation with respect to the position of the first sample 1700 about the Y axis only, and should not include rotation about the X or Z axis, or translation across the X, Y, or Z axis with respect to the position of the first sample 1700.

Upon repeating the test in the negative Z direction, the output data is load versus foot travel distance for the second direction of bending, and is recorded as load $L_2$ vs. travel of foot 1701 $D_2$ from point of contact to test termination. Load $L_2$ and foot travel distance $D_2$ are recorded for at least about every 0.5 millimeters of foot 1701 travel $D_2$, and preferably at least every 0.1 millimeters of travel to create a smooth curve or line.

Calculations

Determine the maximum difference in loads $L_1$ and $L_2$ at any deflection D, where $D_1=D_2$ and the absolute value of the difference between $L_1$ and $L_2$ is a maximum.

To aid in comparison of the results of testing in the positive Z and negative Z directions, it may be useful to place both data sets on one graph of load vs. deflection, such that the load is read along the Y axis of the graph, and the deflection is read along the X axis of the graph. Both data sets can be plotted such that both $L_1$ and $L_2$ are plotted along the Y-axis of the graph, and $D_1$ and $D_2$ are plotted along the X axis.

One suitable way to find the point of maximum difference in the loads for a given deflection is to graphically measure the distance between the $L_1$ and $L_2$ curves along a direction parallel to the Y axis of the graph at multiple points along the load curves. Graphically, this point may be visually apparent, or it may be required to make multiple measurements to ascertain the greatest distance between the lines.

Another suitable way to find the maximum difference in loads for a given deflection is to use a computer or computer software to electronically calculate and find the point of maximum difference between $L_1$ and $L_2$ for a given deflection D, where $D_1=D_2$.

Once the point of maximum difference is obtained, the Percent Load Difference and the point of maximum difference can be calculated with the following formula:

$$\frac{|L_{1d} - L_{2d}|}{L_{3d}} * 100\% = PLD$$

Where:
$L_{1d}$=The load of the sample $L_1$ at the point of maximum difference
$L_{2d}$=The load of the sample $L_2$ at the point of maximum difference
$L_{3d}$=The greater of the two values of $L_{1d}$ or $L_{2d}$, and,
PLD=Percent Load Difference at the point of maximum difference

EXAMPLE

Example 1

A suitable two layer preferential bend structure may be made similar to that shown in FIG. 1G; however the discontinuities are within the auxiliary layer in this example. A base layer may be 20 mm wide (x direction)×60 mm long (y direction)×0.76 mm thick (z direction). The base layer may be a natural polypropylene sheet available from Roberts PolyPro Inc., Charlotte, N.C. under product code F040F-M. The auxiliary layer may comprise twelve segments each having the size 20 mm wide (x direction)×5 mm long (y direction)×0.76 mm thick (z direction). The auxiliary layer may be a natural polypropylene sheet available from Roberts PolyPro Inc., Charlotte, N.C. under product code F040F-M. The twelve auxiliary layer segments may be disposed on the base layer such that the width of each auxiliary layer segment is be arranged along the width of the base layer. The auxiliary layer segment are to be butted together such that line separating each segment is substantially parallel to the x-direction. Once the auxiliary layer segments are disposed on the base layer, the base layer and auxiliary layer should be substantially coterminous. The auxiliary layer may be affixed to the base layer with a suitable hot melt adhesive such as product code H2031 available from ATO Findley Wauwatosa, Wis. The adhesive may be applied at 20 grams/meter$^2$ to the base layer prior to attachment of the auxilary layer Example 2

A suitable two layer preferential bend structure may be made similar to that shown in FIG. 2C. A base layer may be 20 mm wide (x direction)×60 mm long (y direction)×0.76 mm thick (z direction). The base layer may be a natural polypropylene sheet available from Roberts PolyPro Inc., Charlotte, N.C. under product code F040F-M. The intermediate layer may comprise eight segments each having the size 20 mm wide (x direction)×5 mm long (y direction)×0.76 mm thick (z direction). The intermediate layer may be a natural polypropylene sheet available from Roberts PolyPro Inc., Charlotte, N.C. under product code F040F-M. The intermediate layers are disposed on the base layer such that the width of each intermediate layer segment is arranged along the width of the base layer. The intermediate layer segments are spaced on the base layer to maintain a 2 mm separation between segments. The intermediate layer may be affixed to the base layer with a suitable hot melt adhesive such as product code H2031 available from ATO Findley Wauwatosa, Wis. The adhesive may be applied at intermediate layer. No adhesive should be applied to the separations between segments. The auxiliary layer may be 20 mm wide (x direction)×60 mm long (y direction)×0.76 mm thick (z direction). The auxiliary layer may be made from 30 grams/meter$^2$ carded nonwoven available from BBA Nonwovens, Old Hickory, Tenn., under product code 87297. The auxiliary layer may be bonded to the intermediate layer with a suitable hot melt adhesive such as product code H2031 available from ATO Findley Wauwatosa, Wis. The adhesive may be applied at 20 grams/meter$^2$ to the intermediate layer prior to attachment of the Auxiliary layer. No adhesive should be applied to the separations between segments.

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It should be apparent that combinations of such embodiments and features are possible and can result in executions within the scope of this invention. It is therefore intended to cover in the appended claims all such changes and modifications that are within the scope of this invention.

What is claimed is:

1. A disposable absorbent article having a body-facing surface, a garment-facing surface, and at least a first end region, a second end region, and an intermediate region;
wherein at least one of said first end region, second end region, or intermediate region comprises a first preferential bend structure having a first face and an opposing second face, said first preferential bend structure comprising a base layer and an auxiliary layer;
wherein the base layer comprises a material composition having a compressive modulus of $K_{base}$ and a tensile modulus of $T_{base}$;
wherein the auxiliary layer comprises a material composition having a compressive modulus of $K_{aux}$ and a tensile modulus of $T_{aux}$;
wherein a sum of $K_{base}$ and $T_{aux}$ relative to a sum of $K_{aux}$ and $T_{base}$ causes the first preferential bend structure to exhibit a preferential bend wherein a first deforming force applied to the first face results in a first deflection and a second deforming force applied to the second face results in a second deflection which is equal to the first deflection, and wherein the second deforming force is not equal to the first deforming force.

2. The disposable absorbent article of claim 1 further comprising a second preferential bend structure having a first face and an opposing second face, said second preferential bend structure comprising a base layer and an auxiliary layer, wherein a first deforming force applied to the first face results in a first deflection and a second deforming force applied to the second face results in a second deflection which is equal to the first deflection, and wherein the second deforming force is not equal to the first deforming force;
wherein the second preferential bend structure is located in a region, which does not comprise the first preferential bend structure, selected from the first end region, second end region, or intermediate region.

3. The disposable absorbent article of claim 2 wherein the first preferential bend structure exhibits preferential bend toward the body-facing surface of the article and the second preferential bend structure exhibits preferential bend toward the garment-facing surface of the article.

4. The disposable absorbent article of claim 2 wherein the article further comprises a third preferential bend structure having a first face and an opposing second face, said third preferential bend structure comprising a base layer and an auxiliary layer, wherein a first deforming force applied to the first face results in a first deflection and a second deforming force applied to the second face results in a second deflection which is equal to the first deflection, and wherein the second deforming force is not equal to the first deforming force;
wherein the third preferential bend structure is located in a region, which does not comprise the first preferential bend structure or the second preferential bend structure, selected from the first end region, second end region, or intermediate region.

5. The disposable absorbent article of claim 4 wherein the first preferential bend structure is located in said first end region, said second preferential bend structure is located in said second end region, and said third preferential bend structure is located in said intermediate region wherein said third preferential bend structure exhibits a preferential bend toward the garment-facing surface of the article.

6. The disposable absorbent article of claim 4 wherein the first preferential bend structure exhibits a preferential bend about a first axial line, the second preferential bend structure exhibits a preferential bend about a second axial line, and the third preferential bend structure exhibits a preferential bend about a third axial line, wherein the third axial line has a different direction from the first axial line or the second axial line.

7. The disposable absorbent article of claim 2 wherein the first preferential bend structure exhibits a preferential bend about a first axial line and the second preferential bend structure exhibits a preferential bend about a second axial line having a different direction from the first axial line.

8. The disposable absorbent article of claim 1, wherein the first preferential bend structure exhibits a preferential bend toward the body-facing surface of the article.

9. The disposable absorbent article of claim 1, wherein the first preferential bend structure further comprises an intermediate layer disposed between the base layer and the auxiliary layer.

10. The disposable absorbent article of claim 9, wherein the intermediate layer comprises void regions.

11. The disposable absorbent article of claim 10, comprising:
a diaper having opposing longitudinal edges and opposing lateral edges and comprising a topsheet, a backsheet, an absorbent core disposed between the topsheet and the backsheet, wherein the garment-facing surface comprises the backsheet and wherein the body-facing surface comprises the topsheet;
wherein the first preferential bend structure extends laterally between the opposing longitudinal edges of the diaper in the intermediate region and is disposed between the absorbent core and the backsheet; and
wherein upon application of a deforming force, the first preferential bend structure bends laterally across the intermediate region to form a U-shape between the opposing longitudinal edges in the intermediate region and is adapted to collect body exudates between a wearer's crotch region and the absorbent core.

12. The disposable absorbent article of claim 11, wherein the diaper further comprises elasticized leg cuffs disposed along the opposing longitudinal edges, and wherein the elasticized leg cuffs exert the deforming force on the first preferential bend structure to form the U-shape.

13. The disposable absorbent article of claim 10, wherein each void region has a width and a depth, wherein the width is approximately equal to or greater than the depth.

14. The disposable absorbent article of claim 9, wherein the intermediate layer comprises a first void region having a first void width and a first void depth and a second void region having a second void width and a second void depth, wherein the first void region and second void region differ in void width and void depth.

15. The disposable absorbent article of claim 1, wherein the preferential bend structure exhibits a Percent Load Difference of about 10% or greater.

16. The disposable absorbent article of claim 1, wherein the base layer comprises a base material selected from polymeric materials, films, foams, nonwoven webs, woven webs, cellulosic materials, metals, laminates thereof, and combinations thereof and wherein the auxiliary layer comprises an auxiliary material selected from polymeric materials, films, foams, nonwoven webs, woven webs, cellulosic materials, metals, laminates thereof, and combinations thereof.

17. The disposable absorbent article of claim 1, wherein the sum of $K_{base}$ and $T_{aux}$ is greater than the sum of $K_{aux}$ and $T_{base}$.

18. A disposable absorbent article having opposing longitudinal edges and opposing lateral edges, the disposable absorbent article comprising:
a topsheet defining a body-facing surface;
a backsheet connected with the topsheet, the backsheet defining a garment-facing surface;
an absorbent core disposed between the topsheet and the backsheet;
a preferential bend structure comprising a base layer, a second layer, and an auxiliary layer, wherein the second layer is disposed on the base layer and wherein the second layer is disposed between the base layer and the auxiliary layer;
wherein the base layer defines a first surface of the preferential bend structure and the second layer defines a second surface of the preferential bend structure, the second surface opposing the first surface, and wherein the auxiliary layer is joined directly with the second surface;
wherein the preferential bend structure extends laterally between the opposing longitudinal edges;
wherein the second layer comprises a plurality of void regions, each void region having a void opening and defining a void width and a void depth, and wherein the void width varies along the void depth such that a maximum void width is defined at void opening;

wherein each void opening is disposed adjacent the second surface and the auxiliary layer with each void extending into the second layer from the second surface toward the base layer;

wherein a first deforming force applied to the first surface results in a first deflection and the first deforming force applied to the second surface results in a second deflection; and wherein the first deflection is greater than the second deflection;

wherein preferential bend structure is disposed between the absorbent core and the backsheet with the base layer disposed adjacent the backsheet and the auxiliary layer disposed adjacent the absorbent core; and wherein the preferential bend structure bends laterally across an intermediate region to form a U-shape between the opposing longitudinal edges and is adapted to collect body exudates between a wearer's crotch region and the absorbent core.

* * * * *